United States Patent [19]

Nicolaou et al.

[11] Patent Number: 5,504,206
[45] Date of Patent: Apr. 2, 1996

[54] FORMATION OF ESPERAMICIN PRECURSORS

[75] Inventors: Kyriacos C. Nicolaou, La Jolla, Calif.; David A. Clark, Newark, Del.

[73] Assignee: The Scripps Research Institute, La Jolla, Calif.

[21] Appl. No.: 312,106

[22] Filed: Sep. 26, 1994

[51] Int. Cl.⁶ .................................................. C07D 265/12
[52] U.S. Cl. ................................................ 544/69; 544/70
[58] Field of Search ........................................ 544/69, 70

[56] References Cited

U.S. PATENT DOCUMENTS 4,837,206   6/1989   Golik ........................................ 514/25

*Primary Examiner*—Joseph K. McKane
*Attorney, Agent, or Firm*—Donald G. Lewis

[57] ABSTRACT

Intermediates useful in preparing the aglycon or core structure of esperamicin are disclosed, as are methods of making and using the same.

4 Claims, 1 Drawing Sheet

FORMATION OF ESPERAMICIN PRECURSORS

GOVERNMENTAL SUPPORT

This invention was made with support from the Government of the United States of America under National Institutes of health Grant CA46446, and the Government of the United States of America has certain rights in this invention.

TECHNICAL FIELD

The present invention relates generally to intermediates for the antibiotics esperamicin and calicheamicin, and more particularly to intermediates useful for the preparation of esperamicin core portions.

BACKGROUND ART

Esperamicin [Golik et al., *J. Am. Chem. Soc.*, 109:3462 (1987)] and calicheamicin [Lee et al., *J. Am. Chem. Soc.*, 109:3466 (1987)] are antibiotics that contain a complex bicyclic enediyne allylic trisulfide core structure linked through glycosyl bonds to an oligosaccharide chain. These oligosaccharide chains, in turn, contain a number of substituted sugar derivatives which contain a tetrahydropyran ring substituted on the ring both with a sulfur atom and with the oxygen atom of a hydroxylamine group.

The chemical structures of esperamicin $A_I$ and calicheamicin $\gamma_1^I$, are illustrated in FIG. 1 herein. The saccharide ring lettered "B" is the aforesaid sulfur- and O-hydroxylamine-substituted tetrahydropyran derivative.

The saccharide rings of an esperamicin correspond to rings "A" and "E" of the calicheamicin shown in FIG. 1 are substituted similarly, except that the esperamicin ring "E" includes an N-isopropyl group rather than an N-ethyl group. The corresponding "B" ring of an esperamicin contains an S-methyl group rather than a S-(saccharide-substituted)-derivatized benzoyl group (C and D rings) shown in FIG. 1. The structures of esperamicin and some of its derivatives are illustrated in U.S. Pat. No. 4,837,206, whose disclosures are incorporated herein by reference.

The enediyne-containing (aglycon or core) and carbohydrate portions of calicheamicin and esperamicin appear to carry out different roles in the biological activity of those molecules. Thus, the core portion appears to cleave DNA [Zein et al., *Science*, 240:1198 (1988)], whereas the oligosaccharide portion of calicheamicin appears to guide the drug to a double stranded DNA minor groove in which the drug anchors itself on the 5' side of a TCCT sequence, and the core cleaves the DNA. Esperamicins are less sequence specific. [Zein et al., *Science*, 244:697 (1989)].

Studies of the effect on DNA cleavage of derivatization or removal of one or more of the D and E rings of calicheamicin indicate the following: removal of the E ring (amino sugar) provided a drug with the same DNA cleaving specificity as the parent, but having a DNA-cleaving efficiency 2 to 3 orders of magnitude less; acylation of the E ring amine maintained specificity but lowered efficiency; removal of the D ring (terminal rhamnose) maintained specificity, but lowered efficiency 50–100 times; and removal of the D and E rings (terminal rhamnose and amino sugar) resulted in inhibition of cleaving. [Zein et al., *Science*, 244:697 (1989)].

Esperamicin lacks the C and D rings but includes a further complex saccharide structure linked to an additional core hydroxyl group. U.K. Patent Application 2,179,649A reports that acid hydrolysis of esperamicins led to cleavage of that second complex saccharide structure and a resulting esperamicin derivative referred to as BBM-1675C that was about as effective as the starting esperamicin BBM-1675A$_1$ (esperamicin A$_1$), and more so than esperamicin BBM-1675A$_2$ (esperamicin A$_2$) as an antitumor and antimicrobial agent.

U.K. Patent Application 2,179,649A also states that further hydrolysis of esperamicin BBM-1675C led to another esperamicin derivative named BBM-1675D that was also said to be about as effective as esperamicin BBM-1675A$_1$, as an antitumor and antimicrobial agent. The data presented indicate that esperamicin BBM-1675D possessed only two saccharide rings; i.e. those corresponding to the A and E rings of FIG. 1 herein.

The present invention describes the synthesis of certain key intermediates useful in the preparation of the enediyne core structure for esperamicin or a derivative or an analog thereof.

SUMMARY OF THE INVENTION

The present invention contemplates intermediate compounds that are useful in the preparation of the aglycon portion of esperamicin, as well as analogs and derivatives thereof, and methods of preparing the same.

One such contemplated intermediate compound can be represented by Formula I, below:

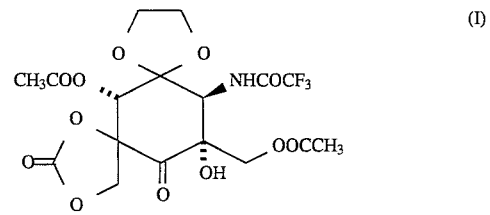

A group of such contemplated compounds can be represented by Formula II, below:

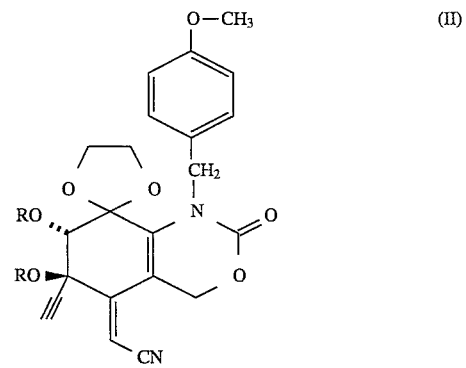

where R is hydrogen or a leaving group.

All of the foregoing compounds are suitable for the preparation of esperamicinone, represented by Formula III, below:

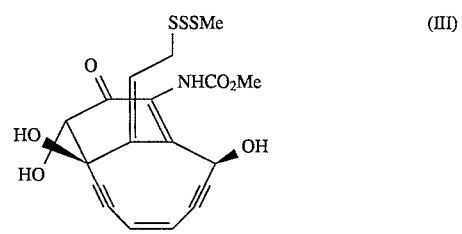

In a method aspect of the present invention, the esperamicinone is produced utilizing the step of an asymmetric epoxidation of a quinone monoketal.

Figure 1:
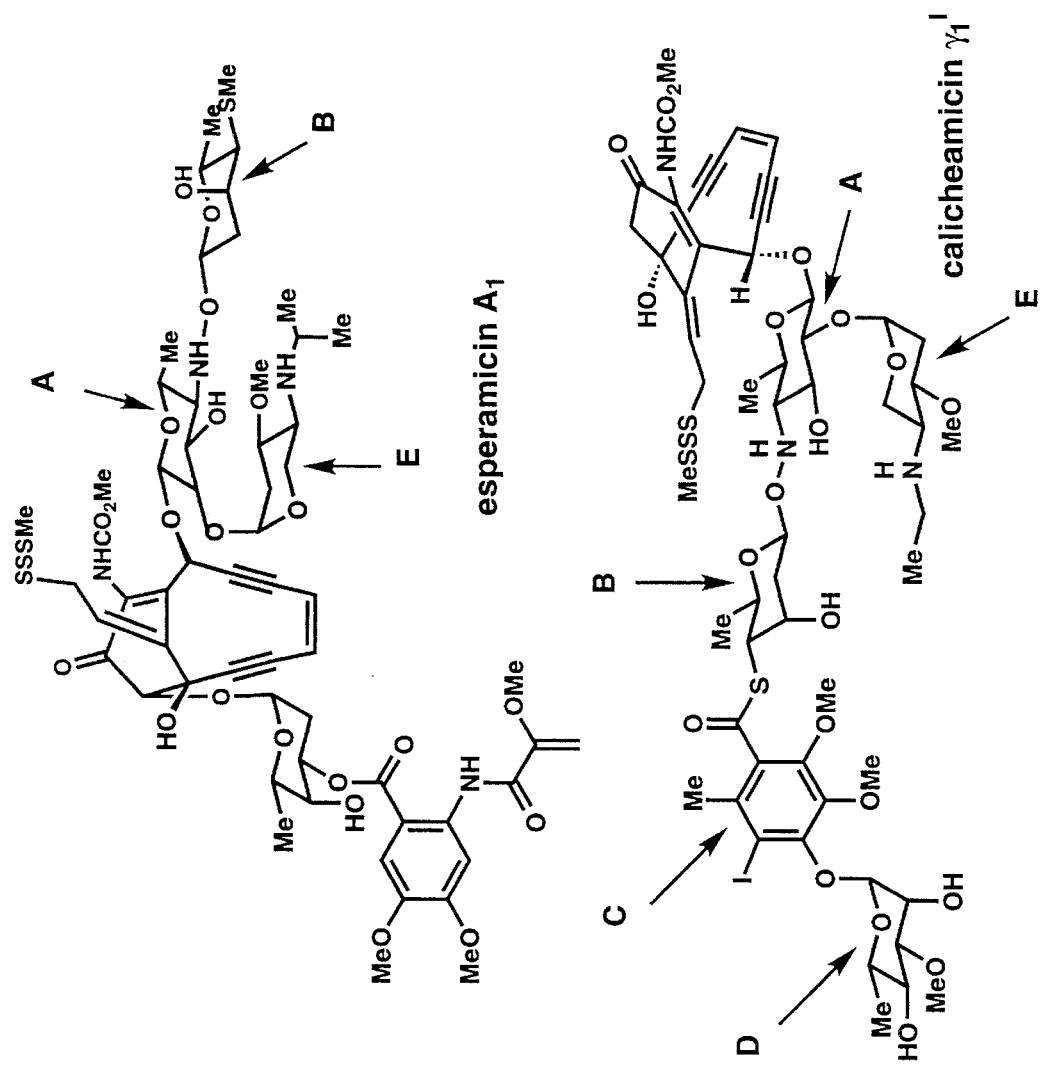
FIG. 1 illustrates the structural formulas for esperamicin $A_1$ and calicheamicin $\gamma_1'$, in which Me is methyl. Hydrogen atoms bonded to ring carbon atoms other than at the glycosidic bond are not shown. The letters A–E designate rings in the oligosaccharide portions.

The stereochemical configuration of saccharide ring substituents is shown as darkened wedge-shaped lines for bonds projecting upwardly from a ring as shown whereas dashes are utilized for bonds that project downwardly from a ring as shown. Ring-bonded hydrogens and hydrogen atoms without stereochemical significance are not shown. Me is methyl and Ph is phenyl in this Figure and all structural formulas where those symbols are utilized.

DESCRIPTION OF PREFERRED EMBODIMENTS

Esperamicin $A_1$ is a member of the enediyne family of antitumor antibiotics exhibiting activity against murine tumor models in the 100 ng/kg range. The family of esperamicins has been isolated from the bacteria *Actinomadura verrucosospora*. Heretofore, synthetic efforts towards esperamicin $A_1$ have mainly been concerned with its saccharide fragments. A new approach to the synthesis of esperamicinone, the aglycon of esperamicin, has now been found.

In accordance with the present invention, esperamicinone 3 is synthesized by means of an asymmetric epoxidation of a quinone monoketal. Two separate approaches are described for the installation of a vinylogous urethane group on the core structure of esperamicinone as is described in greater detail hereinbelow.

Starting with a trihydroxy aromatic compound, such as triol 9, a monoprotected quinone 8 is produced and converted first to an enone epoxide 7 and then to an aziridine 6. From the latter, the synthesis leads ultimately to esperamicinone 3 (Scheme 1).

DEFINITIONS

DIPT—di-isopropyl-D-tartrate

DMAP—p-(dimethylamino)pyridine

DMF—dimethylformamide

KHMDS—potassium bis(trimethylsilyl)amide

MCM—methoxyethoxymethyl

Ms—$SO_2Me$

M.S.—molecular sieve

PMB—p-methoxybenzyl pyr—pyridine

TBS—tert.-butyldimethylsilyl

TES—triethysilyl or $Et_3Si$—

TESOTf—$Et_3Si$—O—$SO_2CF_3$

Tf—$SO_2CF_3$

THF—tetradydrofuran

THP—tetrahydropyranyl

TMS—trimethylsilyl

ONE APPROACH: INTRODUCTION OF NITROGEN BY A 1,4-ADDITION TO AN ENONE

Beginning with the known triol 9 (Scheme 2),

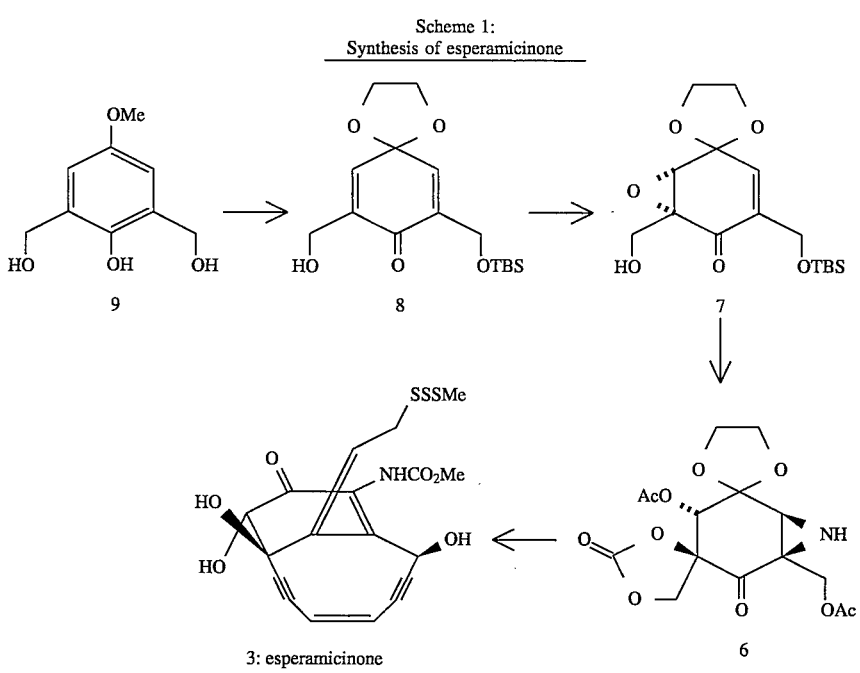

Scheme 2.
Synthesis of intermediate 15.

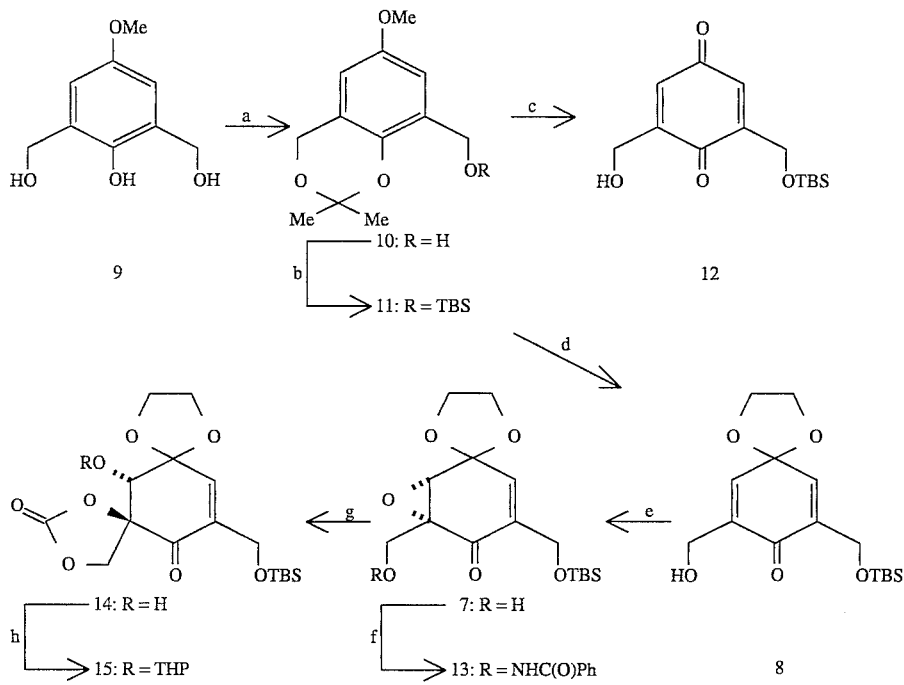

Reagents and conditions:
(a) 0.05 equiv. of TsOH, Me$_2$C(OMe)$_2$/acetone (2:1), 25° C., 1.5 h then AcOH/H$_2$O (1:1), 16 h 77%;
(b) 1.1 equiv of TBSCl, 1.5 equiv of imidazole, 0.05 equiv of DMAP, DMF, 25° C., 1 h, 100%;
(c) 2.1 equiv of Ce(NH$_4$)$_2$(NO$_3$)$_6$, CH$_3$CN, 25° C., 0.2 h, 90%;
(d) 2.05 equiv of Ce(NH$_4$)$_2$(NO$_3$)$_6$, ethylene glycol/1,4-dioxane (1:1), 25° C., 0.2 h, 82%;
(e) 0.1 equiv of Ti(O$^i$Pr)$_4$, 0.125 equiv of DIPT, 2.0 equiv of $^t$BuOOH, 4 Å M.S., CH$_2$Cl$_2$, 0° C., 16 h 87%;
(f) 1.1 equiv of PhNCO, 1.2 equiv of Et$_3$N, CH$_2$Cl$_2$, 25° C., 1 h, 99%;
(g) 1.1 equiv of BF$_3$OEt$_2$, CH$_2$Cl$_2$, 0° C., 0.4 h then AcOH/H$_2$O (8:2), 25° C., 0.3 h, 80%;
(h) 3.0 equiv of dihydropyran, 0.2 equiv of TsOH pyr, CH$_2$Cl$_2$, 25° C., 6 h, 81%.

the primary hydroxyl groups are first differentiated by ketalization (77%) followed by silylation (100%) under standard conditions to afford 11 via 10. Selective protection of the less hindered carbonyl in 12 can be achieved by synthesizing the latter compound by oxidation (ammonium cerium(IV) nitrate) of 11 in aqueous acetonitrile (90% yield). By conducting the oxidation with ethylene glycol as a co-solvent (ammonium cerium(IV) nitrate, 1,4-dioxane/ ethylene glycol (1:1)), the desired monoprotected quinone (8) is obtained directly from 11 in high yield (82%). Quinone monoketals are generally prepared by oxidation of phenols or by partial hydrolysis of bis ketals. Formation of the ketone in this case is a result of acetonide collapse induced by oxidation of the aromatic ring. Simple addition and transketalization of ethylene glycol occurs to form the dioxolane, facilitated by acid catalysis under the reaction conditions.

Sharpless epoxidation of the resultant electron deficient alkene in 8 (Scheme 3) forms epoxide 7 in 87% yield and with acceptable levels of enantioselectivity (80% ee). The enantioselectivity was determined by use of the chiral shift reagent tris [3-(heptafluoropropyl-hydroxy-methylene)-camphorato] europium (III) derivative in C$_6$D$_6$ and observation of the epoxide proton signal [or in the case of (Scheme 11), CHCN] ($^1$H NMR) where baseline resolution could be achieved in a racemic sample. Two recrystallizations of the epoxide from heptane are usually sufficient to enhance the ee to greater than 95%.

Epoxide opening is best effected using the procedure of Roush et al., *J. Org. Chem.*, 45:5083(1980), (Scheme 3; 1. PhNCO, Et$_3$N, CH$_2$Cl$_2$, 99%; 2. BF$_3$.OEt$_2$, CH$_2$Cl$_2$, then HOAc, H$_2$O, 80% yield) which generates the hydroxy carbonate 14. The resulting hindered secondary alcohol can be protected as an acetate (vide infra), or as a triethylsilyl (TES) or a tetrahydropyranyl (THP) ether (15), the latter being most useful despite the formation of a mixture of separable diastereomers (3:1 ratio, 81% yield) due to its stability under the basic conditions used to remove the carbonate group. All subsequent studies described in this section are carried out with the major THP isomer.

The allylic ether present in 15 proved to be particularly labile as the chemistry presented in Scheme 3 demonstrates. With tert.-butyldimethylsilyl (TBS) or methoxyethoxymethyl (MEM) protection, hydrolysis through allylic displacement readily occurs with aqueous NaOH (15 or 18→19, 73%). However, elaboration of the ketone by the requisite two carbon fragment leads to the complete suppression of this allylic lability.

Scheme 3.
Hydrolysis of carbonates 15 and 18.

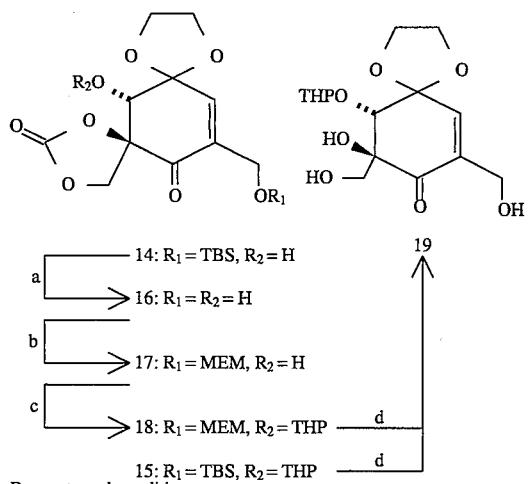

14: R₁ = TBS, R₂ = H
a
16: R₁ = R₂ = H
b
17: R₁ = MEM, R₂ = H
c
18: R₁ = MEM, R₂ = THP —d→ 19
15: R₁ = TBS, R₂ = THP —d→

Reagents and conditions:
(a) excess HF.pyr, THF, 0° C., 0.3 h, 78%;
(b) 1.3 equiv of MEMCl, 1.8 equiv of ⁱPr₂EtN, ClCH₂CH₂Cl, 80° C., 1 h, 77%;
(c) 3.0 equiv of dihydropyran, 0.2 equiv of TsOH.pyr, ClCH₂CH₂Cl, 70° C., 1.5 h, 86°;
(d) 4.0 equiv of NaOH, 1,4-dioxane/H₂O (3:2), 25° C., 0.2h, 73%.

Extension is carried out in two steps (alkylation and dehydration) because Wittig, Peterson and Horner-Emmons reactions are ineffective and because a greater degree of control is provided by a separate dehydration step to influence the ratio of alkene isomers formed. The lithium anion of acetonitrile is generated with ⁿBuLi and condensed with ketone 15 to provide the adduct 24 (Scheme 4) as a single isomer (83%). The facial selectivity of addition is presumed to be that derived from axial attack of the nucleophile to the ring conformation in which the secondary tetrahydropyranyl ether occupies an equatorial position.

Scheme 4.
Synthesis of model alkyne 30.

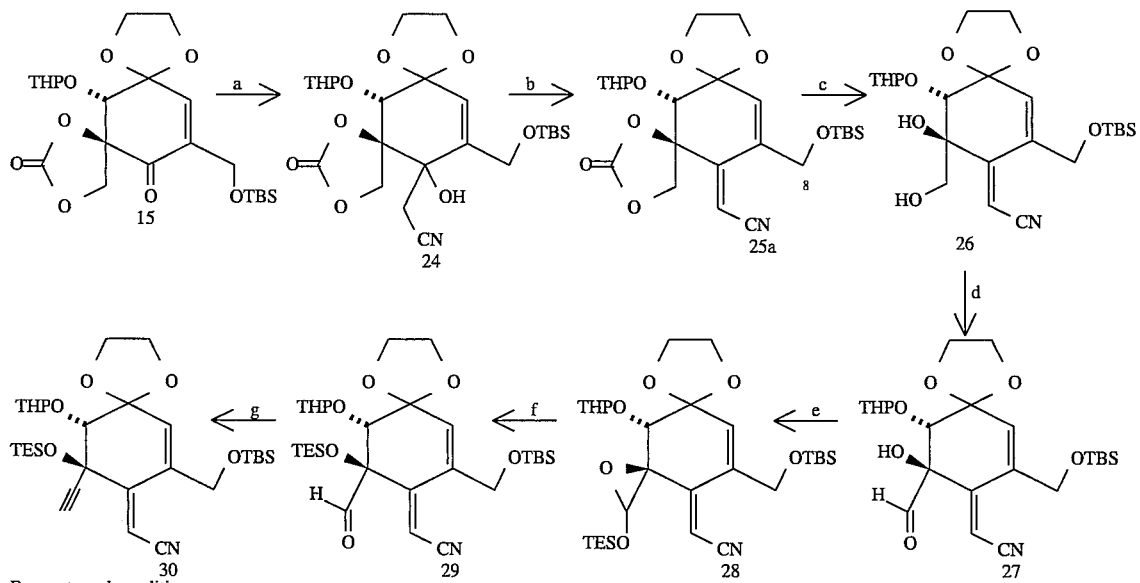

Reagents and conditions:
(a) 1.15 equiv of tBuLi, 1.25 equiv of CH₃CN, THF then 15, −78° C., 0.2 h, 83%;
(b) 1.3 equiv of (CF₃CO)₂O, 2.5 equiv of Et₃N, 0.1 equiv of DMAP, CH₂Cl₂, 25° C., 0.5 h, 83%;
(c) 2.2 equiv of NaOH, 1,4-dioxane/H₂O (7:4), 25° C., 5 h, 100%;
(d) 1.5 equiv of Dess-Martin periodinane, CH₂Cl₂, 25° C., 4 hr, 85%;
(e) 1.2 equiv of TESOTf, 1.5 equiv of 2,6-lutidine, CH₂Cl₂, 25° C., 0.5 h, 74%;
(f) 10 equiv of TESOTf, 15 equiv of 2,6 lutidine, ClCH₂CH₂Cl, 70° C., 1 h, 77%;
(g) 2.5 equiv of (MeO)₂P(O)CHN₂, 1.7 equiv of ⁿBuLi, THF, −78% C., 0.1 h then 29, −78° C. —→ 0° C., 40%.

Dehydration of the tertiary allylic alcohol 24 with trifluoroacetic anhydride gives 25a,b (Scheme 4; 83%) as a 4:1 mixture of geometrical isomers with the desired isomer (25a) predominating. The geometry of the alkenes thus produced is deduced from the downfield shifts of the neighboring methylene proton signals ($^1$H NMR) that are forced into close proximity with the nitrile group (mean values for the chemical shifts are: 25a: 4.58 (carbonate $CH_2$), 4.71 ($CH_2$ OTBS) and 25b: 4.74 (carbonate $CH_2$), 4.25 ($CH_2$ OTBS)).

The carbonate group can be cleanly removed from 25a with aqueous NaOH to afford 26 in quantitative yield (Scheme 4). Dess-Martin oxidation proved to be superior to other methods (e.g. $SO_3$-pyr, Swern) for generation of the hydroxy aldehyde 27 from 26 (85%). Attempted tertiary alcohol protection (TESOTf, 2,6-lutidine) gave the silyloxy epoxide 28 as the initial product (74%), presumably due to the congested environment around the tertiary alcohol. Previous examples of isolable siloxy epoxides were prepared via the epoxidation of silyl enol ethers. However, heating silyl lactol 28 with an excess of TESOTf caused collapse of the lactol, presumably through initial silylation of the epoxide, and produced the desired silyl ether 29 in good yield (77%). Even though this protection could be carried out in a single step with excess reagents and prolonged reaction times, the two step process was more efficient.

Formation of the alkyne 30 from 29 (Scheme 4) was accomplished using the Seyferth reagent $(MeO)_2P(O)CHN$ and either $^n$BuLi or KO$^t$Bu as base.

Next, reaction of 31 with diphenylsulfilimine (PhS=NH) gives the aziridine 32 (Scheme 5) in excellent yield (93%) and as a single isomer. An X-ray crystallographic analysis of the crystalline diacetate 34 (ethyl acetate/petroleum ether, mp 154°–156° C.) indicated that the aziridine was formed on the upper face of the enone:

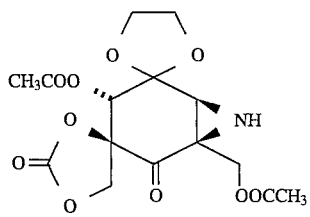

The ring was opened at the tertiary center with the assistance of a neighboring acetate group (Scheme 5, 34→35→36; 80% yield).

Scheme 5.
Ring opening of aziridine 32.

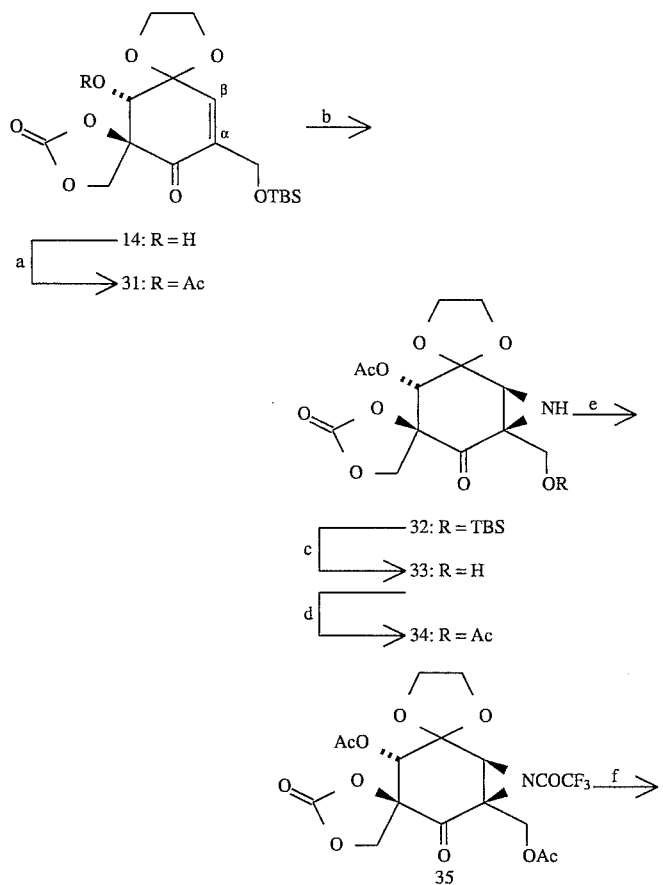

-continued
Scheme 5.
Ring opening of aziridine 32.

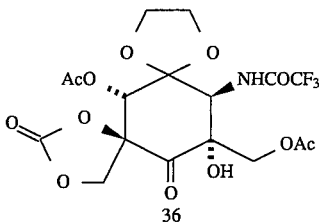

36

Reagents and conditions:
(a) 1.2 equiv of AcCl, 1.3 equiv of DMAP, CH$_2$Cl$_2$, 25° C., 0.5 h, 90%;
(b) 2.0 equiv of Ph$_2$S=NH, C$_6$H$_6$, 55° C., 1 h, 93%;
(c) excess HF.pyr, THF, 0° C., 0.5 h;
(d) 1.3 equiv of Ac$_2$O, 1.6 equiv of pyr, 0.1 equiv of DMAP, CH$_2$Cl$_2$, 25° C., 0.5 h, 90% for two steps;
(e) 1.2 equiv of (CF$_3$CO)$_2$O, 1.5 equiv of Et$_3$N, 0.1 equiv of DMAP, CH$_2$Cl$_2$, 25° C., 1 h;
(f) 0.15 equiv of TsOH, THF/H$_2$O (10:1), 25° C., 1h, 80% for two steps.

ANOTHER APPROACH: INSTALLMENT OF THE NITROGEN AT AN EARLY STAGE

An alternative strategy is to introduce nitrogen onto the aromatic ring at an early stage. Nitration of the hydroxy ketal 10 using nitric acid/acetic acid (Scheme 6) gives the nitro compound 37 and the quinone 38 (ca 60%), the former in relatively low yield.

Scheme 6.
Attempted nitration of acetonide 10.

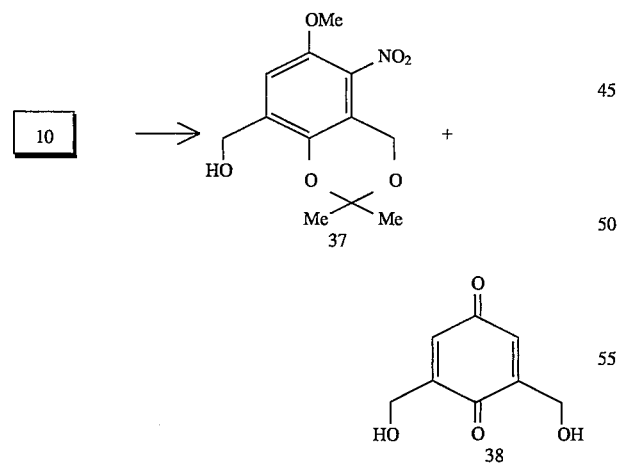

Reagents and conditions:?
(a) 1.0 equiv of HNO$_3$, AcOH, 20–30° C., 0.3 h; 37: 25%, 38: 60%.?

The oxidation process can be suppressed by employing a more stable ketal such as the cyclohexylidene ketal. In such as case, the ratio of products is reversed. With the ethylidene ketal 39, an excellent yield (91%) of the nitro compound 40 is obtained as a single regioisomer (Scheme 7).

Scheme 7.
Synthesis of intermediate 44.

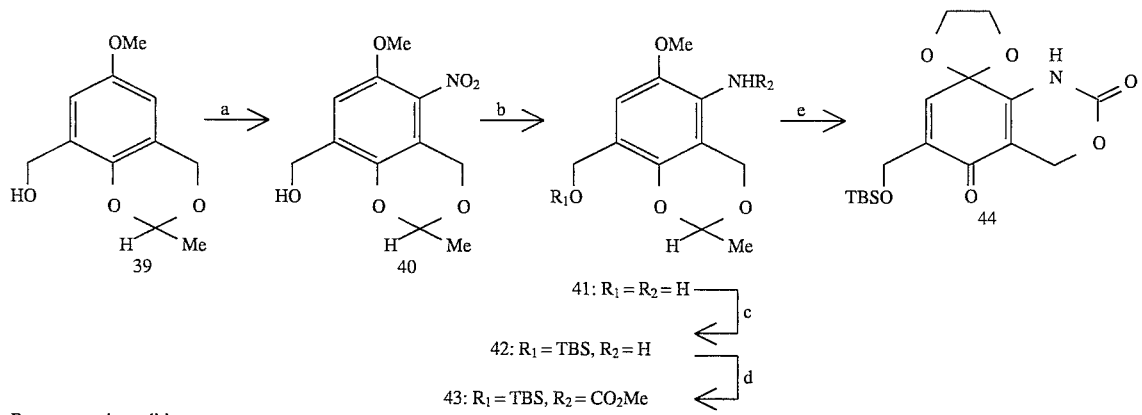

Reagents and conditions:
(a) 1.0 equiv of HNO$_3$, AcOH, 20–30° C., 0.3 h, 91%;
(b) H$_2$, 0.09 equiv of PtO$_2$, 0.08 equiv of K$_2$CO$_3$, MeOH, 25° C., 6 h, 80%;
(c) 1.1 equiv of TBSCl, 1.4 equiv of imidazole, 0.05 equiv of DMAP, DMF, 25° C., 3 h, 95%;
(d) 1.2 equiv of COCl$_2$, 4.0 equiv of Et$_3$N, 0.05 equiv of DMAP, CH$_2$Cl$_2$, 0° C., 0.5 h then excess MeOH, 25° C., 1 h, 72% for two steps;
(e) 2.0 equiv of Ce(NH$_4$)$_2$(NO$_3$)$_6$, ethylene glycol/1,4-dioxane (1:3), 25° C., 1.5 h, then silica gel, CH$_2$Cl$_2$, 25° C., 16 h, 30%.

Reduction of 40 to the aniline 41 is best effected with H$_2$/PtO$_2$ (80%) in the presence of a small amount of potassium carbonate to avoid benzylic hydrogenolysis, especially on a large scale. Silylation under standard conditions (41→42, 95%) is followed by introduction of the urethane using phosgene and methanol (72%) as methyl chloroformate is too unreactive in this case. Oxidation (ammonium cerium (IV) nitrate, ethylene glycol/1,4-dioxane (1:3)) of urethane 43 produces the desired monoprotected quinone 44 but only in 30% yield. The primary hydroxyl group initially produced in this reaction apparently cyclizes onto the urethane system during silica gel chromatography. This cyclization procedure is more conveniently realized prior to purification by stirring the material with silica gel in methylene chloride; most of the desired material may then be purified by crystallization. Although the yield of this process is rather modest, much functionality is being installed in this one step. Large amounts of urethane 43 can readily be prepared as chromatography may be avoided up to this stage.

The chemistry developed for the introduction of the 1,2-diol and alkyne systems is utilized (Scheme 8).

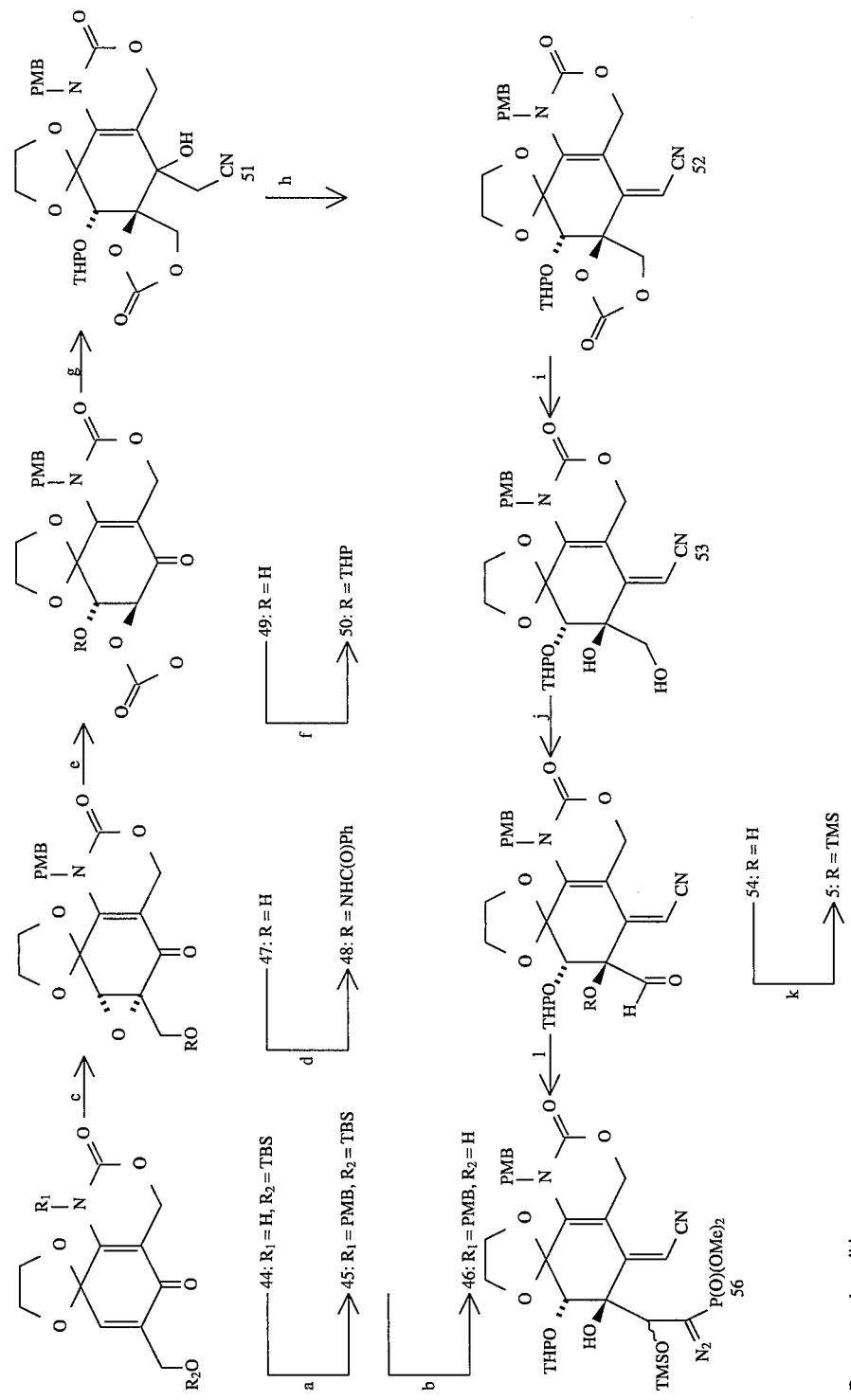

-continued
Scheme 8.
Synthesis of adduct 56.

(i) 1.0 equiv of LiH, ethylene glycol/THF (1:20), 25° C., 1.5 h, 90%;
(j) 2.0 equiv of Dess-Martin periodinane, CH$_3$CN, 25° C., 16 h, 90%;
(k) 10 equiv of TMSOTf, 15 equiv of 2,6-lutidine, ClCH$_2$CH$_2$Cl, 60° C., 4.5 h, 60%;
(l) 1.4 equiv of (MeO)$_2$P(O)CHN$_2$, 1.3 equiv of $^n$BuLi, THF, −78° C., 0.1 h then 55, −78° C. → 25° C., 2 h.

Protection of the cyclic urethane 44 with a p-methoxybenzyl (PMB) group (90%) followed by desilylation with hF.pyridine leads to alcohol 46 (81% overall yield) via intermediate 45. Epoxidation of the allylic alcohol system in 46 using the Sharpless conditions furnishes epoxide 47 (90% yield, 80% ee). A single recrystallization from methanol (20 mL/g) gives optically pure material (60% yield after crystallization, the optical purity confirmed by $^1$H NMR analysis of the R- Mosher ester derivative). Boron trifluoride induced epoxide opening via phenylurethane 48 proceeds smoothly to produce carbonate 49 in 81% overall yield from 47. Protection of the hydroxyl group in 49 as a tetrahydropyranyl ether under standard conditions (49→50; 90% yield, 5:4 ratio of diastereomers) is followed by addition of the lithium anion of acetonitrile to afford hydroxynitrile 51 in 92% yield as a single isomer of unassigned stereochemistry. Dehydration of 51 using acetic anhydride gives exclusively the desired geometrical isomer 52 after five days reaction time. Although aqueous NaOH attacks both the carbonate and the urethane functionalities in 52, excellent selectivity for the carbonate group is observed with lithium hydride in ethylene glycol and THF[5b] (1:20) furnishing the 1,2-diol 53 in 90% yield. Oxidation of the latter compound with the Dess-Martin reagent afforded the hydroxy aldehyde 54 in 90% yield.

The TMS derivative 55 is prepared (without observation of the protected lactol) in 60% yield by exposure of 54 to TMSOTf under basic conditions. The subsequent reaction of 55 with dimethyl diazomethylphosphonate and $^n$BuLi leads to the diazo derivative 56.

The PMB protected urethane 45 is reacted with acetonitrile anion as described above to afford adduct 57 in 82% yield (Scheme 9).

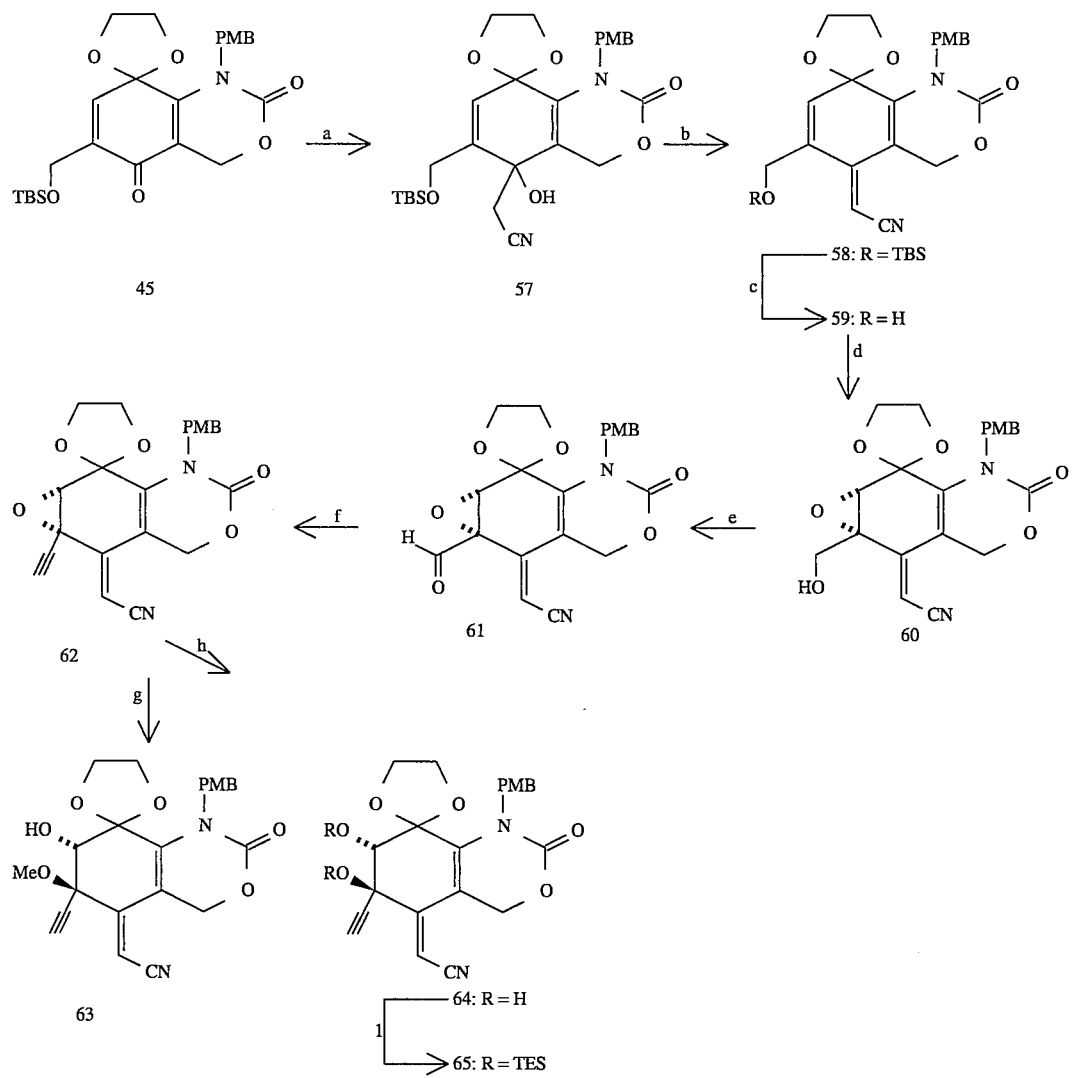

Scheme 9.
Synthesis of diol 64.

Reagents and conditions:
(a) 1.15 equiv of $^t$BuLi, 1.25 equiv of Ch$_3$CN, THF, −78° C. then 45, 0.1 h, 82%;
(b) 1.2 equiv of (CF$_3$CO)$_2$O, 1.4 equiv of Et$_3$N, 0.1 equiv of DMAP, CH$_2$Cl$_2$, 25° C., 0.25 h, 83%;
(c) excess HF pyr, THF, 0° C., 1 h, 96%;
(d) 0.1 equiv of TiO($^i$Pr)$_4$, 0.125 equiv of DIPT, 2.1 equiv of $^t$BuOOH, 4 Å M.S., CH$_2$Cl$_2$, 0° C., 16 h, 86%;

-continued
Scheme 9.
Synthesis of diol 64.

(e) 2.0 equiv of Dess-Martin periodinane, CH$_2$Cl$_2$, 25° C., 36 h, 99%;
(f) 1.4 equiv of (MeO)$_2$P(O)CHN$_2$, 1.2 equiv of $^n$BuLi, THF, 0.1 h, −78° C., then 61, 2.5 h, −78° C. ⟶ 0° C., 50%;
(g) 13 equiv of H$_2$SO$_4$, MeOH, 65° C., 1 h, 72%;
(h) 5 equiv of H$_2$SO$_4$, $^t$BuOH/H$_2$O (1:1), 90° C., 2.5 h, 60%;
(i) 3.1 equiv of TESOTf, 5.1 equiv of pyr, CH$_2$Cl$_2$, 25° C., 1.5 h, 95%.

Exposure of 57 to trifluoroacetic anhydride in the presence of DMAP and Et$_3$N gives the unsaturated nitrile 58 as the major product (83% yield, ca 10:1 ratio with its geometrical isomer). Desilylation of 58 with HF.pyridine under anhydrous conditions proceeds in excellent yield (96%) to afford primary alcohol 59. Asymmetric epoxidation of 59 under the Sharpless conditions proceeds rapidly and in good enantiomeric excess (86% yield, 90% ee) furnishing epoxide 60. Oxidation of 60 to aldehyde 61 was accomplished with the Dess-Martin reagent (99% yield), and alkyne formation with (MeO)$_2$P(O)CHN$_2$ proceeds smoothly to afford compound 62 in 50% yield. Treatment of epoxide 62 with sulfuric acid in methanol at 60° C. produces a single compound (63) and in 72% yield. The regiochemistry of 63 is apparent from observation of two coupled doublets corresponding to the CH and OH of the secondary hydroxyl ($^1$H NMR). The stereochemical assignment is based on published precedent, Battistini et al., *J. Org. Chem.*, 46:434 (1981), and on the apparent absence of a second product. When the solvolysis is conducted in a mixture of 2N aqueous sulfuric acid and tert.-BuOH (1:1) at 90° C., the corresponding diol (64) is formed in 60% yield. The bis(TES) ether 65 is formed from 64 under standard conditions and in 95% yield.

Aromatic system 9 can be converted to a variety of highly functionalized intermediates suitable for elaboration to esperamicinone and related compounds. Advanced intermediates include the aziridine 34, urethane 36, and acetylenes 64 and 65. These and other related compounds are useful in the synthesis of enediyne systems as well as other compounds of medicinal interest.

EXPERIMENTAL SECTION

General Techniques

All reactions described hereinbelow were carried out under a dry argon atmosphere using freshly distilled solvents unless otherwise noted. Tetrahydrofuran and ethyl ether were distilled from sodium and benzophenone. Benzene, methylene chloride and toluene were distilled from calcium hydride. All other anhydrous solvents were purchased from Aldrich Chemical Company Inc. Amine bases were dried and stored over potassium hydroxide. Glassware was either oven dried (120° C.) or flame dried (0.05 torr) prior to use. Where necessary, compounds were dried by azeotropic removal of water with benzene or toluene under reduced pressure. Reactions were monitored by thin layer chromatography (TLC) on E. Merck silica gel plates (0.25 mm) and visualized using uv light (254 nm) and/or heating with p-anisaldehyde solution (340 mL ethanol, 9.2 mL p-anisaldehyde, 12.5 mL sulfuric acid and 3.75 mL acetic acid). Reaction temperatures were measured externally unless otherwise noted. Solvents used for work-up, chromatography, and recrystallizations were reagent grade from either Fisher Scientific or E. Merck. Reactions were worked-up by washing with saturated aqueous solutions of the salts indicated. Flash chromatography was performed on E. Merck silica gel (60, particle size 0.040–0.063 mm). Yields refer to chromatographically and spectroscopically ($^1$H NMR) pure materials.

NMR spectra were recorded on a Bruker AMX-500 MHz spectrometer at ambient temperature. Chemical shifts are reported relative to the residual solvent peak. Multiplicities are designated as singlet (s), doublet (d), triplet (t), pseudo triplet (pt), quartet (q), multiplet (m), broad (b), apparent (app) or obstructed (obs). IR samples were prepared by evaporation of a solution of the compound in CHCl$_3$ or CDCl$_3$ onto a NaCl plate under a stream of argon. IR spectra were recorded on a Perkin Elmer 1600 series FT-IR spectrophotometer. Optical rotations were measured using a Perkin Elmer 241 polarimeter. High resolution mass spectra (HRMS) were recorded on a VG ZAB-ZSE mass spectrometer under Fast Atom Bombardment (FAB) conditions. Melting points were obtained with a Thomas Hoover Unimelt apparatus and are uncorrected. Microanalyses were performed at the Scripps Research Institute.

Preparation of Compounds

Acetonide 10. To a solution of triol 9 (74 g, 400 mmol) in acetone (370 mL) and 2,2-dimethoxypropane (740 mL) was added TsOH (3.8 g, 20.0 mmol) and the reaction mixture was stirred at 20° C. for 0.5 h. Further addition of TsOH (3.8 g) brought the reaction to completion after 1 h at which time the solution was neutralized by the addition of excess solid sodium bicarbonate. The mixture was concentrated under reduced pressure, diluted with ethyl ether (1000 mL) and washed with h$_2$O (4×200 mL). The solution was again concentrated under reduced pressure and acetic acid (24 mL, 50% v/v aqueous solution) was added. The mixture was allowed to stand for 0.5 h before being diluted with ethyl ether (1000 mL), washed with NaHCO$_3$ (5×200 mL), NaCl (200 mL), dried (MgSO$_4$) and concentrated under reduced pressure to yield acetonide 10 (69.6 g, 77%) as a white solid: White crystals (benzene), mp 82.5°–83.0° C.; R$_f$=0.35 (silica gel, 50% ethyl ether in petroleum ether); $^1$H NMR (500 MHz, CDCl$_3$) δ6.77 (d, J=2.9 hz, 1 h, Ar), 6.44 (d, J=2.9 hz, 1 h, Ar), 4.81 (s, 2 h, ring benzylic CH$_2$), 4.62 (s, 2 h, CH$_2$OH), 3.74 (s, 3 h, OCH$_3$), 3.3–2.9 (bs, 1 h, OH), 1.53 (s, 6 h, acetonide); $^{13}$C NMR (125 MHz, CDCl$_3$) δ153.2, 142.8, 129.8, 119.9, 113.1, 108.5, 99.6, 61.3, 61.0, 55.7, 24.8; IR (film) v$_{max}$ 3418, 2993, 2941, 2858, 1612, 1480, 1378, 1283, 1245, 1199, 1145, 1051, 873 cm$^{-1}$; HRMS Calcd. for C$_{12}$H$_{16}$O$_4$ (M+Cs$^+$): 357.0103. Found: 357.0103.

Silyl ether 11. To a solution of 10 (19.7 g, 93.8 mmol) in DMF (188 mL) was added imidazole (9.6 g, 140 mmol), DMAP (507 mg, 4.70 mmol) and TBSCl (15.6 g, 103 mmol). The mixture was stirred at ambient temperature for 1 h before being diluted with ethyl ether (1000 mL), washed with 1N hCl (2×300 mL), NaHCO$_3$ (300 mL), NaCl (300 mL) and dried (MgSO$_4$). The solution was concentrated under reduced pressure and placed under high vacuum (.03 torr, 24 h) to yield silyl ether 11 (30.4 g, 100%) as an off white solid. The material can be recrystallized by dissolving it in ethanol (2 mL/g) and cooling to −20° C. for 24 h: White crystals (ethanol), mp 49.0°–50.0° C.; R$_f$=0.62 (silica gel, 20% ethyl ether in petroleum ether); $^1$H NMR (500 MHz, CDCl$_3$) δ6.97 (d, J=3.0 hz, 1 h, Ar), 6.39 (d, J=3.0 hz, 1 h, Ar), 4.81 (s, 2 h, ring benzylic CH$_2$), 4.69 (s, 2 h, CH$_2$OTBS), 3.76 (s, 3 h, OCH$_3$), 1.51 (s, 6 h, acetonide), 0.96 (s, 9 h, Si$^t$BuMe$_2$), 0.12 (s, 6 h, Si$^t$BuMe$_2$); $^{13}$C NMR (125 MHz, CDCl$_3$) δ153.2, 141.5, 130.7, 119.1, 111.5, 107.3, 99.1, 61.0, 59.5, 55.5, 25.9, 24.7, 18.4, −5.3; IR (film) ν$_{max}$ 2949, 2856, 1612, 1477, 1379, 1247, 1145, 1114, 1058, 841, 779 cm$^{-1}$; HRMS Calcd. for C$_{18}$H$_{30}$O$_4$Si (M+Cs$^+$): 471.0968. Found: 471.0968.

Quinone 12. To a solution of 11 (1.76 g, 5.21 mmol) in acetonitrile (60 mL) and h$_2$O (25 mL) was added ammonium cerium(IV) nitrate (5.97 g, 10.9 mmol). After 0.1 h the solution was diluted with ethyl ether (350 mL), washed with h$_2$O (100 mL), NaHCO$_3$ (2×100 mL), NaCl (100 mL) and dried (MgSO$_4$). The solution was filtered through a pad of silica gel and concentrated under reduced pressure to yield pure quinone 12 (1.32 g, 90%): Yellow solid; R$_f$=0.48 (silica gel, 50% ethyl ether in petroleum ether); $^1$H NMR (500 MHz, CDCl$_3$) δ6.79 (dt, J=2.6(d), 2.4(t) hz, 1 h, vinyl CH), 6.75 (dt, J=2.6(d), 2.0(t) hz, 1 h, vinyl CH), 4.53 (app d, J=2.4 hz, 4 h, allylic CH$_2$), 2.40–2.35 (bs, 1 h, OH), 0.92 (s, 9 h, Si$^t$BuMe$_2$), 0.09 (s, 6 h, Si$^t$BuMe$_2$); $^{13}$C NMR (125 MHz, CDCl$_3$) δ187.8, 187.6, 148.4, 146.9, 131.2, 130.8, 59.3, 59.0, 25.8, 18.2, −5.5; IR (film) ν$_{max}$ 3444, 2932, 2858, 1852, 1465, 1406, 1288, 1258, 1166, 1115, 917, 842, 780 cm$^{-1}$; HRMS Calcd. for C$_{14}$H$_{22}$O$_4$Si (M+Na$^+$): 305.1185. Found: 305.1179.

Quinone monoketal 8. To a solution of 11 (13.98 g, 41.36 mmol) in 1,4-dioxane (105 mL) and ethylene glycol (105 mL) was added ammonium cerium(IV) nitrate (46.5 g, 84.9 mmol). The mixture was stirred at ambient temperature for 0.2 h before being diluted with ethyl ether (500 mL), washed with h$_2$O (200 mL), NaHCO$_3$ (2×100 mL) and dried (MgSO$_4$). The solution was filtered through a pad of silica gel, washing with ethyl ether and concentrated under reduced pressure to give monoketal 8 (10.95 g, 82%) as a yellow oil. A small sample of material was purified by flash chromatography (silica gel, 60% ethyl ether in petroleum ether) for the purpose of data collection: Colorless oil; R$_f$=0.28 (silica gel, 70% ethyl ether in petroleum ether); $^1$H NMR (500 MHz, CDCl$_3$) δ6.66 (dt, J=3.0(d), 2.2 (t) hz, 1 h, vinyl CH), 6.61 (dt, J=3.0 (d), 1.4 (t) hz, 1 h, vinyl CH), 4.41 (d, J=1.4 hz, 2 h, allylic CH$_2$), 4.37 (d, J=2.2 hz, 2 h, allylic CH$_2$), 4.18–4.15 (m, 4 h, ketal), 0.93 (s, 9 h, Si$^t$BuMe$_2$), 0.09 (s, 6 h, Si$^t$BuMe$_2$); $^{13}$C NMR (125 MHz, CDCl$_3$) δ186.0, 138.7, 138.6, 137.7, 137.3, 99.2, 65.8, 60.5, 59.1, 25.9, 18.4, −5.4; IR (film) ν$_{max}$ 3446, 2930, 2858, 1690, 1647, 1465, 1407, 1318, 1256, 1192, 1120, 1086, 969, 840, 779 cm$^{-1}$; HRMS Calcd. for C$_{16}$H$_{26}$O$_5$Si (M+H$^+$): 327.1628. Found: 327.1630

Epoxide 7. A solution of allylic alcohol 8 (10.95 g, 33.6 mmol) in methylene chloride (54 mL) was stirred with pre-dried 4 Å molecular sieves (3.5 g) and di-isopropyl-D-tartrate (0.89 mL, 4.2 mmol) for 3 h at ambient temperature. The solution was cooled to −30° C. and titanium tetraisopropoxide (1.0 mL, 3.36 mmol) was added. The mixture was allowed to warm to −5° C. over 0.5 h before being recooled to −30° C. and treated with tert.-butyl hydroperoxide (12.2 mL, ca 5.5M in methylene chloride, 67.1 mmol). The reaction mixture was stirred for 14 h at 0° C. before being quenched with water (50 mL). The mixture was diluted with ethyl acetate (50 mL) and stirred for 1 h before being filtered through a pad of Celite®, washing with ethyl acetate (500 mL). The layers were separated and the organic phase was washed with Na$_2$S$_2$O$_4$ (2×250 mL, 15% w/w aqueous solution), NaHCO$_3$ (200 mL), NaCl (100 mL) and dried (MgSO$_4$). Concentration under reduced pressure and purification by flash chromatography (silica gel, 50→60% ethyl ether in petroleum ether) gave epoxide 7 (10.02 g, 87%) which solidifies on standing. Optically pure material may be obtained by thrice recrystallizing from heptane (5 mL/g): White plates (heptane), mp 81.0°–81.5° C.; R$_f$=0.28 (silica gel, 70% ethyl ether in petroleum ether); [α]$_D^{25}$ +113.0 (C=0.44, CHCl$_3$); $^1$H NMR (500 MHz, C$_6$D$_6$) δ6.62 (ddd, J=2.9, 2.2, 2.1 hz, 1 h, vinyl CH), 4.53 (dd, J=16.1, 2.2 hz, 1 h, allylic CH$_2$), 4.22 (dd, J=16.1, 2.1 hz, 1 h, allylic CH$_2$), 3.93–3.84 (bm, 2 h, CH$_2$OH), 3.65 (d, J=2.9 hz, 1 h, epoxide CH), 3.49–3.43 (m, 2 h, ketal), 3.39–3.36 (m, 2 h, ketal), 1.64 (bt, 1 h, OH), 0.88 (s, 9 h, Si$^t$BuMe$_2$), −0.07 (s, 6 h, Si$^t$BuMe$_2$); $^{13}$C NMR (125 MHz, CDCl$_3$) δ193.9, 137.9, 135.4, 101.8, 66.1, 66.0, 59.1, 58.7, 58.5, 57.8, 25.8, 18.3, −5.5; IR (film) ν$_{max}$ 3484, 2932, 2890, 2858, 1685, 1466, 1404, 1312, 1256, 1192, 1123, 985, 947, 842, 780 cm$^{-1}$; HRMS Calcd. for C$_{16}$H$_{26}$O$_6$Si (M+Cs$^+$): 475.0553. Found: 475.0559. Anal. Calcd. for C$_{16}$H$_{26}$O$_6$Si: C, 56.12; h, 7.65. Found: C, 55.95; h, 7.70.

Urethane 13. To a solution of epoxide 7 (5.46 g, 16.0 mmol) in methylene chloride (53 mL) was added triethylamine (2.7 mL, 19.4 mmol) and phenyl isocyanate (1.9 mL, 17.5 mmol). After 1 h the reaction mixture was diluted with ethyl ether (200 mL) and washed with 1N hCl (2×50 mL), NaHCO$_3$ (2×50 mL) and dried (MgSO$_4$). Concentration under reduced pressure and purification by flash chromatography (silica gel, 30→40% ethyl ether in petroleum ether) yielded urethane 13 as a white foam (7.26 g, 99%): Colorless oil; R$_f$=0.34 (silica gel, 50% ethyl ether in petroleum ether); [α]$_D^{25}$ +82.0 (C= 4.37, CHCl$_3$); $^1$H NMR (500 MHz, CDCl$_3$) δ7.37–7.35 (bm, 2 h, Ar), 7.31–7.27 (m, 2 h, Ar), 7.07–7.05 (m, 1 h, Ar), 6.87 (bs, 1 h, NH), 6.38 (dt, J=2.8(d), 2.3(t) hz, 1 h, vinyl CH), 4.70 (d, J=12.5 hz, 1 h, CH$_2$OC(O)NHPh), 4.54 (bd, J=12.5 hz, 1 h, CH$_2$OC(O)NHPh), 4.45 (dd, J=16.4, 2.3 hz, 1 h, allylic CH$_2$), 4.21 (dd, J=16.4, 2.3 hz, 1 h, allylic CH$_2$), 4.22–4.10 (m, 4 h, ketal), 3.72 (d, J=2.8 hz, 1 h, epoxide CH), 0.91 (s, 9 h, Si$^t$BuMe$_2$), 0.07 (s, 6 h, Si$^t$BuMe$_2$); $^{13}$C NMR (125 MHz, CDCl$_3$) δ191.8, 152.5, 137.7, 137.4, 135.1, 129.0, 123.6, 118.6, 101.6, 66.1, 66.0, 60.1, 59.1, 58.5, 57.0, 25.8, 18.2, −5.5, −5.6; IR (film) ν$_{max}$ 3335, 2953, 2890, 2857, 1738, 1686, 1602, 1539, 1446, 1316, 1218, 1120, 952, 841, 755 cm$^{-1}$; HRMS Calcd. for C$_{23}$H$_{31}$O$_7$NSi (M+Cs$^+$): 594.0924. Found: 594.0931.

Carbonate 14. To a solution of urethane 13 (7.26 g, 15.7 mmol) in methylene chloride (80 mL) was added boron trifluoride etherate (2.1 mL, 17 mmol). After 0.3 h a solution of acetic acid (8 mL, 80% v/v aqueous solution) in ethyl acetate (80 mL) was added and the mixture was stirred for a further 0.3 h. The reaction mixture was cautiously poured into a saturated aqueous solution of NaHCO$_3$ (300 mL) and stirred for 0.1 h. After dilution with ethyl ether (500 mL), the layers were separated and the organic phase was washed with NaHCO$_3$ (150 mL), NaCl (150 mL) and dried (MgSO$_4$). Concentration under reduced pressure and purification by flash chromatography (silica gel, 40→50% ethyl ether in petroleum ether) gave carbonate 14 (4.85 g, 80%): White solid (methylene chloride/petroleum ether), mp 115.0°–115.5° C.; R$_f$=0.33 (silica gel, 60% ethyl ether in petroleum ether); [α]$_D^{25}$ −6.1 (c=1.57, CHCl$_3$); $^1$H NMR (500 MHz, CDCl$_3$) δ6.77 (t, J=2.1 hz, 1 h, vinyl CH), 4.95 (d, J=9.2 hz, 1 h, carbonate CH$_2$), 4.42 (s, 1 h, CHOH), 4.38 (dd, J=16.5, 2.1 hz, 1 h, allylic CH$_2$), 4.33 (dd, J=16.5, 2.1 hz, 1 h, allylic CH$_2$), 4.33–4.30 (m, 1 h, ketal), 4.21–4.16 (m, 1 h, ketal), 4.15 (d, J=9.2 hz, 1 h, carbonate CH$_2$), 4.12–4.06 (m, 2 h, ketal), 3.95–3.75 (bs, 1 h, OH), 0.91 (s, 9 h, Si$^t$BuMe$_2$), 0.08 (s, 6 h, Si$^t$BuMe$_2$); $^{13}$C NMR (125 MHz, CDCl$_3$) δ191.4, 154.6, 142.1, 138.9, 103.8, 85.1, 71.4, 71.3, 67.2, 67.1, 66.8, 59.0, 25.8, 18.2, −5.5; IR (film) v$_{max}$ 3455, 2953, 2894, 2858, 1814, 1695, 1469, 1391, 1329, 1258, 1095, 1066, 1027, 993, 951, 838, 778 cm$^{-1}$; HRMS Calcd. for C$_{17}$H$_{26}$O$_8$Si (M+Cs$^+$): 519.0451. Found: 519.0459.

THP ether 15. To a solution of alcohol 14 (937 mg, 2.43 mmol) in methylene chloride (12 mL) was added dihydropyran (663 µL, 7.23 mmol) and PPTS (122 mg, 0.49 mmol). After 14 h at ambient temperature, the reaction mixture was diluted with ethyl acetate (40 mL), washed with NaHCO$_3$ (2×15 mL), NaCl (15 mL) and dried (MgSO$_4$). Concentration under reduced pressure and purification by flash chromatography (silica gel, 30→40% ethyl ether in petroleum ether) yielded 15 (627 mg of the more polar isomer and 293 mg of the less polar isomer, 81%). 15 (Less polar isomer): Colorless oil; R$_f$=0.47 (silica gel, 50% ethyl ether in petroleum ether); [α]$_D^{25}$ −39.9 (c=4.80, CHCl$_3$); $^1$H NMR (500 MHz, CDCl$_3$) δ6.76 (t, J=2.1 hz, 1 h, vinyl CH), 4.91 (d, J=9.3 hz, 1 h, carbonate CH$_2$), 4.90–4.88 (m, 1 h, THP anomeric CH), 4.48 (s, 1 h, CHOTHP), 4.37 (dd, J=16.4, 2.1 hz, 1 h, allylic CH$_2$), 4.33 (dd, J=16.4, 2.1 hz, 1 h, allylic CH$_2$), 4.37–4.34 (m, 1 h, ketal), 4.20–4.16 (m, 1 h, ketal), 4.14 (d, J=9.3 hz, 1 h, carbonate CH$_2$), 4.12–4.04 (m, 2 h, ketal), 4.00–3.95 (m, 1 h, THP), 3.55–3.50 (m, 1 h, THP), 1.78–1.70 (m, 2 h, THP), 1.62–1.48 (m, 4 h, THP), 0.89 (s, 9 h, Si$^t$BuMe$_2$), 0.07 (s, 6 h, Si$^t$BuMe$_2$); $^{13}$C NMR (125 MHz, CDCl$_3$) δ191.5, 153.7, 142.7, 138.6, 104.0, 100.0, 85.5, 74.7, 67.6, 67.0, 66.7, 63.0, 58.9, 30.5, 25.8, 25.0, 19.3, 18.2, −5.5; IR (film) v$_{max}$ 2951, 2859, 1821, 1697, 1469, 1394, 1258, 1207, 1135, 1067, 953, 839 cm$^{-1}$; HRMS Calcd. for C$_{22}$H$_{34}$O$_9$Si (M+Cs$^+$): 603.1026. Found: 603.1011.

15 (More polar isomer): White solid; R$_f$=0.37 (silica gel, 50% ethyl ether in petroleum ether); [α]$_D^{25}$ +63.8 (c=3.03, CHCl$_3$); $^1$H NMR (500 MHz, CDCl$_3$) δ6.76 (t, J=2.1 hz, 1 h, vinyl CH), 5.11–5.09 (bm, 1 h, THP anomeric CH), 4.94 (d, J=9.1 hz, 1 h, carbonate CH$_2$), 4.49 (s, 1 h, CHOTHP), 4.37 (d, J=2.1 hz, 2 h, allylic CH$_2$), 4.23–4.19 (m, 1 h, ketal), 4.15 (d, J=9.1 hz, 1 h, carbonate CH$_2$), 4.17–4.11 (m, 1 h, ketal), 4.08–4.02 (m, 2 h, ketal), 3.94–3.88 (m, 1 h, THP), 3.60–3.54 (m, 1 h, THP), 1.80–1.52 (m, 6 h, THP), 0.91 (s, 9 h, Si$^t$BuMe$_2$), 0.08 (s, 6 h, Si$^t$BuMe$_2$); $^{13}$C NMR (125 MHz, CDCl$_3$) δ191.6, 154.0, 142.3, 139.0, 105.0, 99.0, 84.1, 74.1, 67.6, 67.0, 66.2, 61.9, 59.0, 30.4, 25.8, 25.0, 18.4, 18.3, −5.4; IR (film) v$_{max}$ 2953, 2858, 1815, 1694, 1469, 1382, 1257, 1141, 1072, 1032, 951, 839 cm$^{-1}$; HRMS Calcd. for C$_{22}$H$_{34}$O$_9$Si (M+Cs$^+$): 603.1026. Found: 603.1023. Anal. Calcd. for C$_{22}$H$_{34}$O$_9$Si.: C, 56.15; h, 7.28. Found: C, 56.04; h, 7.46.

Diol 16. To a solution of silyl ether 14 (257 mg, 0.666 mmol) in THF (3.3 mL) in a polypropylene vessel at 0° C. was added hydrogen fluoride-pyridine (1.0 mL). The solution was stirred for 0.3 h, diluted with ethyl acetate (40 mL) and poured cautiously into NaHCO$_3$ (50 mL). After 0.1 h of stirring, the layers were separated and the organic phase was washed with NaCl (20 mL) and dried (MgSO$_4$). Concentration under reduced pressure and trituration with ethyl ether (2× 10 mL) gave pure diol 16 (141 mg, 78%): White solid. R$_f$=0.41 (silica gel, ethyl acetate); $^1$H NMR (500 MHz, acetone-d$_6$) δ6.82 (t, J=1.9 hz, 1 h, vinyl CH), 5.68 (d, J=5.7 hz, 1 h, secondary OH), 4.89 (d, J=9.1 hz, 1 h, carbonate CH$_2$), 4.42 (d, J=5.7 hz, 1 h, CHOH), 4.35–4.31 (m, 1 h, ketal), 4.29–4.25 (m, 4 h, carbonate CH$_2$, CH$_2$OH and ketal), 4.20–4.09 (m, 3 h, ketal and primary OH); $^{13}$C NMR (125 MHz, acetone-d$_6$) δ192.9, 154.8, 142.8, 139.8, 105.0, 86.0, 71.8, 67.7, 67.2, 54.5; IR (film) v$_{max}$ 3282, 3020, 2921, 1812, 1692, 1381, 1127, 1071, 1030, 990, 954 cm$^{-1}$; HRMS Calcd. for C$_{11}$H$_{12}$O$_8$ (M+H$^+$): 273. 0610. Found: 273.0607.

MEM ether 17. To a solution of diol 16 (137 mg, 0.504 mmol) in 1,2-dichloroethane (2.5 mL) was added diisopropylethylamine (158 µL, 0.907 mmol) and MEM chloride (75 µL, 0.65 mmol) and the mixture was refluxed for 1 h. After cooling to ambient temperature the solution was diluted with ethyl acetate (40 mL), washed with 1N hCl (15 mL), NaHCO$_3$ (15 mL) and NaCl (15 mL). The aqueous phases were extracted with methylene chloride (50 mL) and the combined organic phase was dried (MgSO$_4$). Concentration under reduced pressure and purification by flash chromatography (silica gel, 20% acetone in chloroform) gave pure MEM ether 17 (140 mg, 77%): White solid; R$_f$=0.23 (silica gel, 20% acetone in chloroform); $^1$H NMR (500 MHz, CDCl$_3$) δ6.78 (t, J=1.7 hz, 1 h, vinyl CH), 4.92 (d, J=9.2 hz, 1 h, carbonate CH$_2$), 4.74, (s, 2 h, OCH$_2$O), 4.39 (d, J=5.4 hz, 1 h, CHOH), 4.31–4.26 (m, 1 h, ketal), 4.26 (d, J=1.7 hz, 2 h, allylic CH$_2$), 4.16 (d, J=5.4 hz, 1 h, OH), 4.14 (d, J=9.2 hz, 1 h, carbonate CH$_2$), 4.18–4.13 (m, 1 h, ketal), 4.10–4.04 (m, 2 h, ketal), 3.69–3.66 (m, 2 h, MEM OCH$_2$CH$_2$O), 3.55–3.52 (m, 2 h, MEM OCH$_2$CH$_2$O), 3.36 (s, 3 h, OCH$_3$); $^{13}$C NMR (125 MHz, CDCl$_3$) δ191.2, 154.4, 143.6, 136.0, 103.7, 95.4, 85.0, 71.6, 71.0, 67.2, 67.1, 66.9, 66.7, 63.0, 59.0; IR (film) v$_{max}$ 3414, 2892, 1807, 1699, 1470, 1374, 1090, 1057 cm$^{-1}$; HRMS Calcd. for C$_{15}$H$_{20}$O$_{10}$ (M+Na$^+$): 383.0954. Found: 383.0960.

THP ether 18. To a solution of alcohol 17 (140 mg, 0.39 mmol) in 1,2-dichloroethane (1.9 mL) was added dihydropyran (106 µL, 1.17 mmol) and PPTS (20 mg) and the mixture was heated at 70° C. for 1.5 h. After cooling to ambient temperature the mixture was diluted with ethyl acetate (40 mL), washed with NaHCO$_3$ (15 mL), NaCl (15 mL) and dried (MgSO$_4$). Concentration under reduced pressure and purification by flash chromatography (silica gel, 80% ethyl ether in petroleum ether then ethyl ether) gave the less polar isomer (49 mg) and the more polar isomer (99 mg) (86% total yield of 18). 18 (More polar isomer).: Colorless oil; R$_f$=0.36 (silica gel, ethyl ether); $^1$H NMR (500 MHz, CDCl$_3$) δ6.78 (t, J=1.7 hz, 1 h, vinyl CH), 5.11–5.09 (m, 1 h, THP anomeric CH), 4.94 (d, J=9.1 hz, 1 h, carbonate CH$_2$), 4.77, (s, 2 h, OCH$_2$O), 4.50 (s, 1 h, CHOTHP), 4.29 (d, J=1.7 hz, 2 h, allylic CH$_2$), 4,17 (d, J=9.1 hz, 1 h, carbonate CH$_2$), 4.21–4.10 (m, 2 h, ketal), 4.09–4.01 (m, 2 h, ketal), 3.93–3.88 (m, 1 h, THP), 3.70–3.68 (m, 2 h, MEM OCH$_2$CH$_2$O), 3.59–3.54 (m, 3 h, MEM OCH$_2$CH$_2$O and THP), 3.39 (s, 3 h, OCH$_3$), 1.80–1.50 (m, 6 h, THP); $^{13}$C NMR (125 MHz, CDCl$_3$) δ191.3, 154.0, 143.6, 136.2, 104.9, 99.0, 95.5, 84.1, 73.9, 71.6, 67.5, 67.2, 67.0, 66.2, 62.9, 61.9, 59.1, 30.4, 25.0, 18.4; IR (film) v$_{max}$ 2945, 2894, 1816, 1696, 1469, 1378, 1063, 956 cm$^{-1}$; HRMS Calcd. for C$_{20}$H$_{28}$O$_{11}$ (M+Na$^+$): 467.1529. Found: 467.1540.

Triol 19. To a solution of carbonate 18 (80 mg, 18 µmol) in 1,4-dioxane (2.0 mL) and water (1.0 mL) was added sodium hydroxide (80 µL, 1N aqueous solution, 80 µmol). After 0.2 h the mixture was diluted with ethyl acetate (50 mL), washed with h$_2$O (20 mL), NaCl (20 mL) and dried (MgSO$_4$). Concentration under reduced pressure and purification by flash chromatography (silica gel, ethyl acetate) gave triol 19 (32 mg, 73%): Colorless oil; R$_f$=0.19 (silica gel, ethyl acetate); $^1$H NMR (500 MHz, CDCl$_3$) δ6.55 (t, J=1.5 hz, 1 h, vinyl CH), 4.65 (bs, 1 h, tertiary OH), 4.64–4.62 (m, 1 h, THP anomeric CH), 4.39 (dd, J=15.0, 1.5 hz, 1 h, allylic CH$_2$), 4.32 (dd, J=15.0, 1.5 hz, 1 h, allylic CH$_2$), 4.20–4.02 (m, 5 h, ketal and THP), 4.12 (s, 1 h, CHOTHP), 3.97 (d, J=11.8 hz, 1 h, CH$_2$OH), 3.82 (d, J=11.8 hz, 1 h, CH$_2$OH), 3.55–3.49 (m, 1 h, THP), 3.0–2.8 (bs, 1 h, OH), 2.4–2.1 (bs, 1 h, OH), 1.90–1.50 (m, 6 h, THP); $^{13}$C NMR (125 MHz, CDCl$_3$) δ197.9, 139.2, 138.9, 104.5, 102.6, 82.5, 78.7, 67.0, 65.8, 65.2, 64.8, 59.9, 31.1, 24.6, 20.8; IR (film) $v_{max}$ 3418, 2945, 1686, 1445, 1385, 1353, 1123, 1029, 974, 912 cm$^{-1}$; HRMS Calcd. for $C_{15}H_{22}O_8$ (M+Na$^+$): 353.1212. Found: 353.1204.

Acetonitrile adduct 24. To a solution of tert.-butyl lithium (154 μL, 1.7M in pentane, 262 μmol) in THF (2.3 mL) at −78° C. was added acetonitrile (15 μL, 0.29 mmol). After 90 s, a solution of ketone 15 (107 mg, 0.23 mmol) in THF (0.5 mL) was added via cannula. After a further 0.1 h, the reaction was quenched by the addition of a saturated solution of ammonium chloride and the mixture was warmed to ambient temperature. The mixture was diluted with ethyl acetate (50 mL), the aqueous phase was separated and the organic layer was washed with NaCl (20 mL) and dried (MgSO$_4$). Concentration under reduced pressure and purification by flash chromatography (silica gel, 60% ethyl ether in petroleum ether) gave adduct 24 (96 mg, 83%): Colorless oil; $R_f$=0.22 (silica gel, 60% ethyl ether in petroleum ether); $[\alpha]_D^{25}$ +96.5 (C=1.57, CHCl$_3$); $^1$H NMR (500 MHz, CDCl$_3$) δ5.54 (s, 1 h, OH), 5.54 (app s, 1 h, vinyl CH), 4.99–4.97 (m, 1 h, THP anomeric CH), 4.91 (d, J=8.6 hz, 1 h, carbonate CH$_2$), 4.75 (dd, J=13.1, 1.3 hz, 1 h, CH$_2$OTBS), 4.40 (d, J=8.6 hz, 1 h, carbonate CH$_2$), 4.37 (s, 1 h, CHOTHP), 4.28 (dd, J=13.1, 0.8 hz, 1 h, CH$_2$OTBS), 4.15–4.06 (m, 2 h, THP and/or ketal), 3.99–3.84 (m, 3 h, THP and/or ketal), 3.60–3.55 (m, 1 h, THP), 3.17 (d, J=16.8 hz, 1 h, CH$_2$CN), 2.92 (d, J=16.8 hz, 1 h, CH$_2$CN), 1.8–1.5 (m, 6 h, THP), 0.90 (s, 9 h, Si$^t$BuMe$_2$), 0.14 (s, 3 h, Si$^t$BuMe$_2$), 0.12 (s, 3 h, Si$^t$BuMe$_2$); $^{13}$C NMR (125 MHz, CDCl$_3$) δ154.2, 136.7, 127.4, 116.6, 105.3, 98.7, 87.3, 75.8, 72.8, 66.7, 65.7, 65.0, 64.8, 61.8, 30.3, 26.9, 25.6, 24.9, 18.2, 18.0, −5.6, −5.7; IR (film) $v_{max}$ 3385, 2950, 2892, 2859, 2254, 1808, 1468, 1391, 1257, 1184, 1075, 1030, 960, 838, 778, 732 cm$^{-1}$; HRMS Calcd. for $C_{24}H_{37}O_9$NSi (M+H$^+$): 512.2316. Found: 512.2320.

Alkenes 25a and 25b. To a solution of adduct 24 (506 mg, 0.99 mmol) in methylene chloride (5 mL) was added triethylamine (343 μL, 2.48 mmol), DMAP (12 mg, 0.1 mmol) and trifluoroacetic anhydride (182 μL, 1.29 mmol). After 0.5 h, the reaction mixture was diluted with ethyl ether (50 mL), washed with 1N hCl (2×20 mL), NaHCO$_3$ (20 mL), NaCl (20 mL) and dried (MgSO$_4$). Concentration under reduced pressure and purification by flash chromatography (silica, 40→50% ethyl ether in petroleum ether) gave compound 25a (450 mg, 91%). Further elution with 70% ethyl ether in petroleum ether gave the isomer 25b (30 mg, 6%).

25a: Colorless oil; $R_f$=0.54 (silica gel, 5% acetone in chloroform); $[\alpha]_D^{25}$ +129.7 (c=1.59, CHCl$_3$); $^1$H NMR (500 MHz, CDCl$_3$) δ6.11 (ddd, J=1.9, 1.7, 1.4 hz, 1 h, ring vinyl CH), 5.74 (d, J=1.4 hz, 1 h, CHCN), 5.20 (d, J=8.9 hz, 1 h, carbonate CH$_2$), 5.04–5.01 (m, 1 h, THP anomeric CH), 4.82 (dd, J=14.9, 1.9 hz, 1 h, CH$_2$OTBS), 4.60 (dd, J=14.9, 1.7 hz, 1 h, CH$_2$OTBS), 4.31 (s, 1 h, CHOTHP), 4.18–4.10 (m, 2 h, THP and/or ketal), 4.00–3.90 (m, 3 h, THP and/or ketal), 3.96 (d, J=8.9 hz, 1 h, carbonate CH$_2$), 3.59–3.54 (m, 1 h, THP), 1.8–1.5 (m, 6 h THP), 0.91 (s, 9 h, Si$^t$BuMe$_2$), 0.11 (s, 3 h, Si$^t$BuMe$_2$), 0.11 (s, 3 h, Si$^t$BuMe$_2$); $^{13}$C NMR (125 MHz, CDCl$_3$) δ153.4, 151.4, 135.1, 131.6, 116.2, 105.1, 98.9, 93.5, 83.9, 74.7, 69.6, 66.8, 65.1, 62.0, 61.5, 30.3, 25.8, 25.0, 18.3, −5.4, −5.5; IR (film) $v_{max}$ 3061, 2951, 2894, 2858, 2218, 1820, 1598, 1469, 1382, 1257, 1203, 1145, 1078, 1035, 955, 910, 837, 780, 733 cm$^{-1}$; HRMS Calcd. for $C_{24}H_{35}O_8$NSi (M+Cs$^+$): 626.1186. Found: 626.1191. 25b: Colorless oil; $R_f$=0.24 (silica gel, 60% ethyl ether in petroleum ether); $[\alpha]_D^{25}$ +40.9 (c=3.97, CHCl$_3$); $^1$H NMR (500 MHz, CDCl$_3$) δ6.06–6.05 (m, 1 h, ring vinyl CH), 5.70 (s, 1 h, CHCN), 5.30 (d, J=8.8 hz, 1 h, carbonate CH$_2$), 5.12–5.10 (m, 1 h, THP anomeric CH), 4.35 (s, 1 h, CHOTHP), 4.26 (dd, J=13.7, 1.4 hz, 1 h, CH$_2$OTBS), 4.23 (dd, J=13.7, 1.4 hz, 1 h, CH$_2$OTBS), 4.17 (d, J=8.8 hz, 1 h, carbonate CH$_2$), 4.15–4.08 (m, 2 h, ketal), 4.03–3.93 (m, 3 h, THP and ketal), 3.59–3.54 (m, 1 h, THP), 1.8–1.5 (m, 6 h THP), 0.89 (s, 9 h, Si$^t$BuMe$_2$), 0.07 (s, 6 h, Si$^t$BuMe$_2$); $^{13}$C NMR (125 MHz, CDCl$_3$) δ153.5, 153.3, 135.3, 133.3, 114.7, 104.9, 98.7, 96.5, 82.9, 74.1, 70.7, 66.8, 65.3, 62.1, 61.9, 30.4, 25.7, 24.9, 18.3, −5.4; IR (film) $v_{max}$ 3061, 2951, 2893, 2858, 2216, 1818, 1591, 1470, 1382, 1253, 1204, 1152, 1077, 1034, 954, 840, 780, 732 cm$^{-1}$; HRMS Calcd. for $C_{24}H_{35}O_8$NSi (M+H$^+$): 494.2210. Found: 494.2210.

Diol 26. To a solution of carbonate 25a (450 mg, 0.91 mmol) in dioxane (3.5 mL) was added sodium hydroxide (2 mL, 1N aqueous solution, 2.0 mmol) . After stirring for 1 h at ambient temperature, the reaction mixture was diluted with ethyl acetate (50 mL), washed with h$_2$O (2×20 mL), NaCl (20 mL) and dried (MgSO$_4$). Concentration under reduced pressure and purification by flash chromatography (silica, 60% ethyl ether in petroleum ether) gave diol 26 (400 mg, 94%): Colorless oil; $R_f$=0.60 (silica gel, 80% ethyl ether in petroleum ether); $[\alpha]_D^{25}$ +138.2 (c=5.03, CHCl$_3$); $^1$H NMR (500 MHz, CDCl$_3$) δ6.05 (ddd, J=2.1, 1.8, 1.3 hz, 1 h, ring vinyl CH), 5.93 (d, J=1.3 hz, 1 h, CHCN), 5.04 (s, 1 h, tertiary OH), 4.92 (dd, J=15.3, 2.1 hz, 1 h, CH$_2$OTBS), 4.51 (dd, J=15.3, 1.8 hz, 1 h, CH$_2$OTBS), 4.46–4.43 (m, 1 h, THP anomeric CH), 4.12–3.93 (m, 5 h, THP and ketal), 3.89 (s, 1 h, CHOTHP), 3.73 (d, J=11.6 hz, 1 h, CH$_2$OH), 3.56 (d, J=11.6 hz, 1 h, CH$_2$OH), 3.54–3.49 (m, 1 h, THP), 2.5–2.4 (bs, 1 h, CH$_2$OH), 1.89–1.77 (m, 2 h, THP), 1.60–1.45 (m, 4 h, THP), 0.90 (s, 9 h, Si$^t$BuMe$_2$), 0.08 (s, 3 h, Si$^t$BuMe$_2$), 0.08 (s, 3 h, Si$^t$BuMe$_2$); $^{13}$C NMR (125 MHz, CDCl$_3$) δ155.2, 137.3, 128.6, 117.7, 104.7, 103.8, 94.2, 85.2, 76.0, 67.0, 66.5, 66.2, 65.6, 61.5, 31.4, 25.8, 24.6, 21.4, 18.2, −5.5, −5.5; IR (film) $v_{max}$ 3405, 2950, 2859, 2213, 1592, 1465, 1404, 1359, 1257, 1206, 1126, 1071, 1034, 973, 838, 780, 733 cm$^{-1}$; HRMS Calcd. for $C_{23}H_{37}O_7$NSi (M+Cs$^+$): 600.1394. Found: 600.1411. Anal. Calcd. for $C_{23}H_{37}O_7$NSi: C, 59.11; h, 7.92; N, 3.00. Found: C, 59.43; h, 7.70; N, 2.87.

Aldehyde 27. To a solution of diol 26 (330 mg, 0.71 mmol) in methylene chloride (3.5 mL) was added Dess-Martin periodinane (450 mg, 1.07 mmol) and the reaction mixture was stirred for 48 h at ambient temperature. The mixture was diluted with ethyl ether (50 mL), filtered through a pad of silica gel, concentrated under reduced pressure and purified by flash chromatography (silica gel, 30→40% ethyl ether in petroleum ether) to yield aldehyde 27 as a clear oil (310 mg, 94%): White solid; $R_f$=0.61 (silica gel, 60% ethyl ether in petroleum ether); $[\alpha]_D^{25}$ +112.6 (C=1.35, CHCl$_3$); $^1$H NMR (500 MHz, CDCl$_3$) δ9.58 (s, 1 h, CHO), 6.21 (ddd, J=2.1, 1.8, 1.3 hz, 1 h, ring vinyl CH), 5.94 (d, J=1.3 hz, 1 h, CHCN), 5.54 (s, 1 h, tertiary OH), 4.96 (dd, J=15.3, 2.1 hz, 1 h, CH$_2$OTBS), 4.60 (dd, J=15.3, 1.8 hz, 1 h, CH$_2$OTBS), 4.56 (dd, J=6.8, 2.3 hz, 1 h, THP anomeric CH), 4.14–3.99 (m, 5 h, THP and ketal), 4.02 (s, 1 h, CHOTHP), 3.60–3.55 (m, 1 h, THP), 1.87–1.76 (m, 2 h, THP), 1.64–1.51 (m, 4 h, THP), 0.93 (s, 9 h, Si$^t$BuMe$_2$), 0.12 (s, 3 h, Si$^t$BuMe$_2$), 0.12 (s, 3 h, Si$^t$BuMe$_2$); $^{13}$C NMR (125 MHz, CDCl$_3$) δ195.5, 150.4, 137.2, 130.4, 117.3, 104.4, 102.8, 95.4, 85.9, 81.6, 67.1, 66.3, 65.4, 61.5, 31.2, 25.9, 24.7, 20.6, 18.3, −5.4, −5.5; IR (film) $v_{max}$ 3337, 3057, 2950, 2859, 2214, 1733, 1591, 1466, 1356, 1259, 1202, 1126, 1033, 957, 837, 780 cm$^{-1}$; HRMS Calcd. for $C_{23}H_{35}O_7$NSi (M+Cs$^+$): 598.1237. Found: 598.1234.

Silyloxy epoxide 28. To a solution of hydroxy aldehyde 27 (65 mg, 0.14 mmol) in 1,2-dichloroethane (700 μL) was added 2,6-lutidine (17 μL, 0.21 mmol) and TESOTf (38 μL, 0.17 mmol). After 0.5 h, the reaction mixture was diluted with ethyl ether (20 mL), washed with $CuSO_4$ (5 mL), $NaHCO_3$ (5 mL) and dried ($MgSO_4$). Concentration under reduced pressure and purification by flash chromatography (silica gel, 10→15% ethyl ether in petroleum ether) gave silyl lactol 28 (62 mg, 77%): Colorless oil; $R_f$=0.48 (silica gel, 30% ethyl ether in petroleum ether); $[\alpha]_D^{25}$ +86.2 (C=2.53, $CHCl_3$); $^1H$ NMR (500 MHz, $C_6D_6$) δ6.42 (ddd, J=2.0, 1.8, 1.3 hz, 1 h, ring vinyl CH), 5.74 (d, J=1.3 hz, 1 h, CHCN), 5.40 (s, 1 h, CHOTES), 5.10–5.08 (m, 1 h, THP anomeric CH), 5.03 (dd, J=15.2, 2.0 hz, 1 h, $CH_2OTBS$), 4.85 (dd, J=15.2, 1.8 hz, 1 h, $CH_2OTBS$), 4.38 (s, 1 h, CHOTHP), 4.28–4.22 (m, 1 h, ketal or THP), 3.61–3.44 (m, 5 h, ketal and THP), 1.80–1.69 (m, 1 h, THP), 1.53–1.24 (m, 5 h, THP), 0.95 (s, 9 h, $Si^tBuMe_2$), 0.92 (t, J=8.0 hz, 9 h, $Si(CH_2CH_3)_3$), 0.55 (q, J=8.0 hz, 6 h, $Si(CH_2CH_3)_3$), 0.08 (s, 3 h, $Si^tBuMe_2$), 0.06 (s, 3 h, $Si^tBuMe_2$); $^{13}C$ NMR (125 MHz, $C_6D_6$) δ147.2, 137.9, 131.3, 117.8, 107.2, 98.4, 94.5, 79.0, 73.3, 66.4, 65.7, 65.2, 62.2, 60.9, 30.7, 26.1, 25.7, 18.7, 18.5, 6.6, 4.8, −5.4; IR (film) $v_{max}$ 3054, 2952, 2883, 2211, 1590, 1464, 1412, 1256, 1191, 1123, 1038, 961, 835, 781, 742 $cm^{-1}$; LRMS Calcd. for $C_{29}H_{49}O_7NSi_2$ $(M+Cs^+)$: 712. Found: 712.

Aldehyde 29. To a solution of protected lactol 28 (50 mg, 86 μmol) in 1,2-dichloroethane (4.3 mL) was added 2,6-lutidine (151 μL, 1.29 mmol), and TESOTf (195 μL, 0.86 mmol) and the mixture was placed in an oil bath at 70° C. After 1 h the mixture was cooled, diluted with ethyl ether (40 mL), washed with $CuSO_4$ (10 mL), $NaHCO_3$ (10 mL) and dried ($MgSO_4$). Concentration under reduced pressure and purification by preparative TLC (silica gel, 30% ethyl ether in petroleum ether) gave the silyl ether 29 (37 mg, 74%): Colorless oil; $R_f$=0.58 (silica gel, 30% ethyl ether in petroleum ether); $[\alpha]_D^{25}$ +161.8 (c=0.50, $CHCl_3$); $^1H$ NMR (500 MHz, $CDCl_3$) δ9.40 (s, 1 h, CHO), 6.19 (ddd, J=2.2, 1.9, 1.2 hz, 1 h, ring vinyl CH), 5.58 (d, J=1.2 hz, 1 h, CHCN), 5.27 (pt, J=5.4 hz, 1 h, THP anomeric CH), 5.04 (dd, J=15.6, 2.2 hz, 1 h, $CH_2OTBS$), 4.56 (dd, J=15.6, 1.9 hz, 1 h, $CH_2OTBS$), 4.20–4.15 (m, 1 h, ketal), 4.12–4.06 (m, 3 h, ketal), 4.04 (s, 1 h, CHOTHP), 3.65–3.61 (m, 2 h, THP), 1.96–1.90 (m, 2 h, THP), 1.65–1.53 (m, 4 h, THP), 0.96 (t, J=8.0 hz, 9 h, $Si(CH_2CH_3)_3$), 0.93 (s, 9 h, $Si^tBuMe_2$), 0.60 (q, J=8.0 hz, 6 h, $Si(CH_2CH_3)_3$), 0.13 (s, 3 h, $Si^tBuMe_2$), 0.13 (s, 3 h, $Si^tBuMe_2$); $^{13}C$ NMR (125 MHz, $C_6D_6$) δ191.8, 149.8, 139.2, 131.1, 116.3, 108.9, 102.9; 93.2, 87.5, 86.0, 66.3, 65.5, 62.1, 61.4, 34.4, 32.4, 25.6, 20.8, 18.1, 6.7, 4.4, −5.7, −5.8; IR (film) $v_{max}$ 2954, 2877, 2218, 1733, 1462, 1377, 1254, 1151, 1103, 1043, 838, 779, 743 $cm^{-1}$; HRMS Calcd. for $C_{29}H_{49}O_7NSi_2$ $(M+Cs^+)$: 712.2102. Found: 712.2111.

Alkyne 30. To a solution of dimethyl diazomethylphosphonate (12 μL, 100 μmol) in THF (0.5 mL) at −78° C. was added $^n$butyl lithium (27 μL, 2.5M in hexane, 64 μmol). After 0.1 h, a solution of 29 (23 mg, 40 μmol) in THF (0.5 mL) was added. The reaction mixture was allowed to warm to −5° C. over 1.5 h before being quenched with a saturated solution of ammonium chloride (5 mL) and diluted with ethyl ether (20 mL). The layers were separated and the organic phase was washed with $NaHCO_3$ (5 mL) and dried ($MgSO_4$). Concentration under reduced pressure and purification by preparative TLC (30% ethyl ether in petroleum ether) gave pure alkyne 30 (9 mg, 40%): Colorless oil; $R_f$=0.60 (silica gel, 30% ethyl ether in petroleum ether); $[\alpha]_D^{25}$ +139 (c=0.27, $CHCl_3$); $^1H$ NMR (500 MHz, $CDCl_3$) δ6.14 (ddd, J=2.1, 1.9, 1.3 hz, 1 h, ring vinyl CH), 5.67 (d, J=1.3 hz, 1 h, CHCN), 5.21 (pt, J=5.3 hz, 1 h, THP anomeric CH), 4.91 (dd, J=15.2, 2.1 hz, 1 h, $CH_2OTBS$), 4.53 (dd, J=15.2, 1.9 hz, 1 h, $CH_2OTBS$), 4.22–4.18 (m, 2 h, ketal), 4.15–4.10 (m, 1 h, ketal), 4.04–3.99 (m, 1 h, ketal), 3.75 (s, 1 h, CHOTHP), 3.64–3.60 (m, 2 h, THP), 2.54 (s, 1 h, CCH), 1.98–1.90 (m, 2 h, THP), 1.65–1.52 (m, 4 h, THP), 0.96 (t, J=8.0 hz, 9 h, $Si(CH_2CH_3)_3$), 0.92 (s, 9 h, $Si^tBuMe_2$), 0.60 (q, J=8.0 hz, 6 h, $Si(CH_2CH_3)_3$), 0.11 (s, 3 h, $Si^tBuMe_2$), 0.11 (s, 3 h, $Si^tBuMe_2$); $^{13}C$ NMR (125 MHz, $CDCl_3$) δ152.5, 137.7, 131.1, 116.4, 108.8, 102.7, 91.2, 84.7, 80.9, 76.6, 76.2, 75.7, 67.1, 65.0, 62.5, 61.6, 34.5, 32.5, 25.8, 20.6, 18.3, 6.8, 4.4, −5.4, −5.4; IR (film) $v_{max}$ 3311, 3274, 2954, 2877, 2219, 2116, 1462, 1259, 1101, 1041, 838, 779, 742 $cm^{-1}$; HRMS Calcd. for $C_{30}H_{49}O_6NSi_2$ $(M+H^+)$: 576.3177. Found: 576.3180.

Acetate 31. To a solution of secondary alcohol 14 (415 mg, 1.08 mmol) in methylene chloride (2.2 mL) was added DMAP (171 mg, 1.40 mmol) and acetyl chloride (97 μL, 1.30 mmol) and the reaction mixture was stirred for 0.5 h at ambient temperature. The mixture was diluted with ethyl ether (30 mL), washed with 1N hCl (10 mL), $NaHCO_3$ (10 mL) and dried ($MgSO_4$). Concentration under reduced pressure and purification by flash chromatography (silica gel, 50→60% ethyl ether in petroleum ether) gave acetate 31 (414 mg, 90%): White crystals (methylene chloride/petroleum ether), mp 137.5°–138.0° C.; $R_f$=0.39 (silica gel, 80% ethyl ether in petroleum ether); $[\alpha]_D^{25}$ +3.1 (c=1.07, $CHCl_3$); $^1H$ NMR (500 MHz, $CDCl_3$) δ6.81 (t, J=2.1 hz, 1 h, vinyl CH), 5.80 (s, 1 h, CHOAc), 4.85 (d, J=9.5 hz, 1 h, carbonate $CH_2$), 4.40 (dd, J=16.8, 2.1 hz, 1 h, allylic $CH_2$), 4.36 (dd, J=16.8, 2.1 hz, 1 h, allylic $CH_2$), 4.22 (d, J=9.5 hz, 1 h, carbonate $CH_2$), 4.19–4.12 (m, 2 h, ketal), 4.09–3.99 (m, 2 h, ketal), 2.18 (s, 3 h, acetate), 0.91 (s, 9 h, $Si^tBuMe_2$), 0.09 (s, 3 h, $Si^tBuMe_2$), 0.09 (s, 3 h, $Si^tBuMe_2$); $^{13}C$ NMR (125 MHz, $CDCl_3$) δ190.2, 168.4, 153.2, 141.5, 139.1, 103.5, 83.0, 69.3, 67.5, 66.8, 66.4, 58.9, 25.8, 20.6, 18.3, −5.5, −5.5; IR (film) $v_{max}$ 2951, 2856, 1823, 1763, 1692, 1468, 1376, 1327, 1262, 1223, 1143, 1107, 1061, 1030, 998, 951, 836, 782 $cm^{-1}$; HRMS Calcd. for $C_{19}H_{28}O_9Si$ $(M+H^+)$: 429.1581. Found: 429.1580.

Aziridine 32. To a solution of enone 31 (424 mg, 0.99 mmol) in benzene (5.0 mL) was added diphenylsulfilimine (398 mg, 1.98 mmol) and the mixture was heated at 55° C. for 1 h before being cooled, concentrated under reduced pressure and purified by flash chromatography (silica gel, 80% ethyl ether in petroleum ether) to yield aziridine 32 (410 mg, 93%): White crystals (methylene chloride/petroleum ether), mp 168.0°–168.5° C.; $R_f$=0.31 (silica gel, 80% ethyl ether in petroleum ether); $[\alpha]_D^{25}$ +9.4 (c=0.34, $CHCl_3$); $^1H$ NMR (500 MHz, $CDCl_3$) δ6.16 (s, 1 h, CHOAc), 4.70 (d, J=9.3 hz, 1 h, carbonate $CH_2$), 4.20 (d, J=9.3 hz, 1 h, carbonate $CH_2$), 4.15–4.03 (m, 4 h, ketal), 4.10 (d, J=11.1 hz, 1 h, $CH_2OTBS$), 4.00 (d, J=11.1 hz, 1 h, $CH_2OTBS$), 2.73 (s, 1 h, aziridine CH), 2.14 (s, 3 h, acetate), 2.0 (bs, 1 h, NH), 0.87 (s, 9 h, $Si^tBuMe_2$), 0.08 (s, 3 h, $Si^tBuMe_2$), 0.07 (s, 3 h, $Si^tBuMe_2$); $^{13}C$ NMR (125 MHz, $CDCl_3$) δ199.7, 168.2, 153.4, 106.5, 83.0, 68.1, 67.5, 66.9, 66.6, 56.2, 45.1, 40.1, 25.7, 20.7, 18.1, −5.5, −5.5; IR (film) $v_{max}$ 3288, 2953, 2859, 1820, 1762, 1732, 1470, 1374, 1219, 1163, 1100, 1061, 909, 838, 782, 733 $cm^{-1}$; HRMS Calcd. for $C_{19}H_{29}O_9NSi$ $(M+H^+)$: 444.1690. Found: 444.1690. Anal. Calcd. for $C_{19}H_{29}O_9NSi$: C, 51.45; h, 6.59; N, 3.16. Found: C, 51.42; h, 6.59; N, 3.15.

Alcohol 33. To a solution of silyl ether 32 (390 mg, 0.88 mmol) in THF (4.4 mL) in a polypropylene vessel at 0° C. was added hydrogen fluoride-pyridine (1.3 mL). The cooling bath was removed and after 0.25 h the mixture was poured cautiously into $NaHCO_3$ (60 mL), diluted with ethyl acetate (120 mL) and stirred for 0.1 h. The layers were separated and the organic phase was washed with $NaHCO_3$ (40 mL), NaCl (40 mL) and dried ($MgSO_4$). The solution was concentrated under reduced pressure to a small volume and petroleum ether (15 mL) was added dropwise. The white solid was collected by filtration (270 mg): White crystals (ethyl acetate); mp 179.5°–181.0° C. (dec); $R_f$=0.29 (silica gel, ethyl acetate); $[\alpha]_D^{25}$ +15.3 (C=0.7, $CHCl_3$); $^1$H NMR (500 MHz, DMSO-$d_6$) δ5.72 (bs, 1 h, CHOAc), 5.11 (t, J=5.9 hz, 1 h, OH), 4.64 (d, J=9.6 hz, 1 h, carbonate $CH_2$), 4.40 (d, J=9.6 hz, 1 h, carbonate $CH_2$), 4.15–3.98 (m, 5 h, ketal and $CH_2OH$), 3.41–3.34 (bm, 1 h, $CH_2OH$), 3.26 (bd, J=7.6 hz, 1 h, NH), 2.82 (bd, J=7.6 hz, 1 h, aziridine CH), 2.14 (s, 3 h, acetate); $^{13}$C NMR (125 MHz, DMSO-$d_6$) δ199.1, 169.0, 153.2, 105.8, 83.3, 66.9, 66.1, 66.1, 57.4, 45.0, 41.0, 20.4; IR (film) $v_{max}$ 3335, 3264, 2965, 2902, 1795, 1752, 1483, 1427, 1379, 1328, 1220, 1176, 1056, 1022, 969 cm$^{-1}$; HRMS Calcd. for $C_{13}H_{15}O_9N$ (M+Cs$^+$): 461.9801. Found: 461.9809.

Acetate 34. To a solution of alcohol 33 (270 mg, 0.88 mmol) in methylene chloride (4.1 mL) was added pyridine (106 µL, 1.41 mmol), DMAP (10 mg, 0.09 mmol) and acetic anhydride (101 µL, 1.14 mmol). The reaction mixture was stirred for 0.5 h before being diluted with ethyl acetate (50 mL), washed with 1N hCl (2×20 mL), $NaHCO_3$ (20 mL), NaCl (20 mL) and dried ($MgSO_4$). The solution was concentrated under reduced pressure to a small volume and petroleum ether was added dropwise. The white solid (34) was collected by filtration (294 mg, 90% for two steps): White crystals (ethyl acetate/petroleum ether); mp 154.0°–156.0° C.; $R_f$=0.41 (silica gel, ethyl acetate); $[\alpha]_D^{25}$ +7.75 (C=2.34, $CHCl_3$); $^1$H NMR (500 MHz, $CDCl_3$) δ6.02 (s, 1 h, CHOAc), 4.68 (d, J=9.4 hz, 1 h, carbonate $CH_2$), 4.56 (d, J=12.2 hz, 1 h, $CH_2OAc$), 4.27 (bd, J=12.2 hz, 1 h, $CH_2OAc$), 4.21 (d, J=9.4 hz, 1 h, carbonate $CH_2$), 4.15–4.00 (m, 4 h, ketal), 2.88 (s, 1 h, aziridine CH), 2.13 (s, 3 h, acetate), 2.2–2.0 (bs, 1 h, NH), 2.07 (s, 3 h, acetate); $^{13}$C NMR (125 MHz, $CDCl_3$) δ197.8, 170.5, 168.4, 153.3, 105.8, 82.9, 67.9, 67.0, 66.6, 61.2, 43.5, 42.5, 20.6; IR (film) $v_{max}$ 3288, 2990, 2903, 1816, 1750, 1474, 1432, 1374, 1221, 1166, 1060, 912, 731 cm$^{-1}$; HRMS Calcd. for $C_{15}H_{17}O_{10}N$ (M+Cs$^+$): 503.9907. Found: 503.9910.

Trifluoroacetate 35. To a solution of aziridine 34 (429 mg, 1.16 mmol) in methylene chloride (5.8 mL) was added triethylamine (242 µL, 1.74 mmol), DMAP (14 mg, 0.12 mmol), and trifluoroacetic anhydride (196 µL, 1.41 mmol). The reaction mixture was stirred for 1 h before being diluted with ethyl acetate (50 mL), washed with 1N hCl (10 mL), $NaHCO_3$ (10 mL), NaCl (10 mL), dried ($MgSO_4$) and concentrated under reduced pressure. The unstable product was immediately subjected to the following reaction. A small sample was purified by flash chromatography (silica gel, 20% acetone in chloroform) for the purpose of data collection: Colorless oil; $R_f$=0.55 (silica gel, 30% acetone in chloroform); $^1$H NMR (500 MHz, $C_6D_6$) δ5.57 (s, 1 h, CHOAc), 4.45 (q, J=1.3 hz, 1 h, aziridine CH), 4.04 (s, 2 h, $CH_2OAc$), 3.89 (d, J=9.6 hz, 1 h, carbonate $CH_2$), 3.74 (d, J=9.6 hz, 1 h, carbonate $CH_2$), 3.31–3.14 (m, 4 h, ketal), 1.55 (s, 3 h, acetate), 1.41 (s, 3 h, acetate); $^{13}$C NMR (125 MHz, $C_6D_6$) δ194.1, 169.5, 167.5, 152.6, 104.2, 89.4, 82.2, 72.8, 71.1, 67.4, 67.4, 66.1, 63.3, 53.5, 29.4, 19.5; IR (film) $v_{max}$ 2967, 2915, 1823, 1756, 1701, 1379, 1216, 1168, 1064, 757 cm$^{-1}$; HRMS Calcd. for $C_{17}H_{16}O_{11}NF_3$ (M+H$^+$): 468.0754. Found: 468.0750.

Tertiary alcohol 36. To a sample of crude aziridine 35 (530 mg), in THF (5 mL) and water (0.5 mL) was added TsOH (30 mg, 0.16 mmol). After stirring for 1 h, the reaction mixture was diluted with ethyl acetate (50 mL), washed with $NaHCO_3$ (10 mL), NaCl (10 mL) and dried ($MgSO_4$). Concentration under reduced pressure and purification by flash chromatography (silica gel, 20→30% acetone in chloroform) yielded 36 (449 mg, 80% for two steps): Colorless oil; $R_f$=0.23 (silica gel, 30% acetone in chloroform); $[\alpha]_D^{25}$ +70.9 (c=0.74, $CHCl_3$); $^1$H NMR (500 MHz, $CDCl_3$) δ7.50 (d, J=9.6 hz, 1 h, NH), 5.97 (s, 1 h, CHOAc), 4.92 (bs, 1 h, tertiary OH), 4.73 (d, J=9.3 hz, 1 h, carbonate $CH_2$), 4.59 (d, J=9.3 hz, 1 h, carbonate $CH_2$), 4.44 (d, J=9.6 hz, 1 h, CHNHCOCF$_3$), 4.37 (d, J.=11.9 hz, 1 h, $CH_2OAc$), 4.25 (d, J=11.9 hz, 1 h, $CH_2OAc$), 4.14–4.02 (m, 4 h, ketal), 2.17 (s, 3 h, acetate), 2.06 (s, 3 h, acetate); $^{13}$C NMR (125 MHz, $CDCl_3$) δ195.7, 170.4, 169.0, 157.8 (app d, J =37.9 hz), 152.8, 116.8, 114.5, 112.2, 105.0, 82.9, 75.8, 69.1, 67.5, 67.1, 66.0, 63.8, 53.2, 30.9, 29.1, 20.5, 20.5; IR (film) $v_{max}$ 3326, 3106, 2978, 2907, 1816, 1730, 1547, 1377, 1218, 1165, 1065, 913, 733 cm$^{-1}$; HRMS Calcd. for $C_{17}H_{18}O_{12}NF_3$ (M+H$^+$): 486.0859. Found: 486.0860.

Ketal 39. To a solution of 9 (220 g, 1.20 mol) in benzene (2.4 L) was added anhydrous copper sulfate (48 g, 300 mmol), acetaldehyde (134 mL, 2.40 mol) and Amberlyst-15 (22 g) . The mixture was stirred at ambient temperature for 5 h before being filtered and concentrated under reduced pressure. Acetic acid (460 mL) and water (200 mL) were added and the mixture was left to stand for 14 h. The mixture was then diluted with ethyl ether (2.0 L), washed with 2N NaOH (4×500 mL) and NaCl (500 mL). The aqueous phases were extracted with methylene chloride (2×500mL) and the combined organic phases were dried ($MgSO_4$) and concentrated under reduced pressure. The solid was recrystallized from methylene chloride (350 mL) and petroleum ether (500 mL) to give ketal 39 (174 g) . A second crop yielded a further 32.2 g (87% total yield): White crystals (ethyl ether); mp 99°–100° C.; $R_f$=0.46 (silica gel, 80% ethyl ether in petroleum ether); $^1$H NMR (500 MHz, $CDCl_3$) δ6.77 (d, J=2.9 hz, 1 h, Ar), 6.42 (d, J=2.9 hz, 1 h, Ar), 5.14 (q, J=5.1 hz, 1 h, OCHO), 4.97 (d, J=14.6 hz, 1 h, ring benzylic $CH_2$), 4.78 (d, J=14.6 hz, 1 h, ring benzylic $CH_2$), 4.65 (d, J=13.1 hz, 1 h, $CH_2OH$), 4.62 (d, J=13.1 hz, 1 h, $CH_2OH$), 3.74 (s, 3 h, $OCH_3$), 2.30 (s, 1 h, OH), 1.54 (d, J=5.1 hz, 3 h, CHCH$_3$); $^{13}$C NMR (125 MHz, $CDCl_3$) δ153.6, 144.5, 129.4, 121.1, 112.8, 108.6, 97.0, 66.3, 60.9, 55.6, 20.6; IR (film) $v_{max}$ 3449, 2942, 2867, 1611, 1481, 1404, 1220, 1102, 1048 cm$^{-1}$; HRMS Calcd. for $C_{11}H_{14}O_4$ (M+Cs$^+$): 342.9946. Found: 342.9952.

Nitrobenzene derivative 40. To a solution of ketal 39 (213 g, 1.01 mol) in acetic acid (1.0 L) was added nitric acid (71 mL, 15.8M) in a dropwise fashion over a period of 0.2 h. A large exotherm at the midpoint of the addition was controlled with an ice bath such that the internal temperature did not exceed 30° C. Shortly after completion of the addition, the product precipitated. The mixture was stirred for a further 0.2 h and filtered. The solid was washed with $h_2O$ (1.5 L) and the mother liquor was further diluted with $h_2O$ (1 L) and cooled to −20° C. for 4 h. A second crop of product was thus recovered, washed with $h_2O$ (1 L) and the combined solid was dried in vacuo to give 40 (233 g, 90%). The material can be recrystallized from methylene chloride (10mL/g) and petroleum ether (20 mL/g): Yellow crystals (methylene chloride), mp 145.5°–146.0° C.; $R_f$=0.36 (silica gel, 80% ethyl ether in petroleum ether); $^1$H NMR (500 MHz, $CDCl_3$) δ7.08 (s, 1 h, Ar), 5.17 (q, J=5.1 hz, 1 h, OCHO), 5.02 (d, J=15.8 hz, 1 h, ring benzylic $CH_2$), 4.79 (d, J=15.8 hz, 1 h, ring benzylic $CH_2$), 4.74 (d, J=14.5 hz, 1 h, $CH_2OH$), 4.70 (d, J=14.5 hz, 1 h, $CH_2OH$), 3.89 (s, 3 h, $OCH_3$), 2.11 (bs, 1 h, OH), 1.56 (d, J=5.1 hz, 3 h, CHCH$_3$);

$^{13}$C NMR (125 MHz, CDCl$_3$) δ146.2, 143.6, 136.2, 133.3, 115.2, 111.2, 97.3, 64.1, 60.0, 57.0, 20.5; IR (film) ν$_{max}$ 3518, 2901, 1610, 1600, 1518, 1459, 1407, 1348, 1293, 1227, 1093 cm$^{-1}$; HRMS Calcd. for C$_{11}$H$_{13}$NO$_6$ (M+Cs$^+$): 387.9797. Found: 387.9800. Anal. Calcd. for C$_{11}$H$_{13}$NO$_6$: C, 51.77; h, 5.13; N, 5.49. Found: C, 51.92; h, 5.11; N, 5.26.

Aniline derivative 41. To a solution of 40 (61 g, 240 mmol) in methanol (2.8 L) was added potassium carbonate (2.8 g, 20 mmol) and platinum oxide (500 mg, 22 mmol). The vessel was evacuated (20 torr) and flushed with argon three times. The reaction mixture was then stirred vigorously under an atmosphere of hydrogen (1–2 atm) until TLC analysis (ethyl ether) indicated that the reaction was complete. The mixture was filtered through a pad of silica gel and concentrated under reduced pressure. Crystallization from ethyl acetate (300 mL) gave aniline derivative 41 as an off white solid (43 g, 80%): White solid (ethyl acetate/ petroleum ether); mp 125.5°–126.0° C.; R$_f$=0.33 (silica gel, ethyl ether); $^1$H NMR (500 MHz, CDCl$_3$) δ6.69 (s, 1 h, Ar), 5.09 (q, J=5.1 hz, 1 h, OCHO), 479 (d, J=14.2 hz, 1 h, ring benzylic CH$_2$), 4.72 (d, J=14.2 hz, 1 h, ring benzylic CH$_2$), 4.61 (d, J=12.3 hz, 1 h, CH$_2$OH), 4.56 (d, J=12.3 hz, 1 h, CH$_2$OH), 3.81 (s, 3 h, OCH$_3$), 3.8–2.5 (bs, 3 h, NH$_2$ and OH), 1.55 (d, J=5.1 hz, 3 h, CHCH$_3$); $^{13}$C NMR (125 MHz, CDCl$_3$) δ145.2, 140.8, 131.5, 117.0, 110.1, 107.0, 96.4, 63.7, 60.8, 56.1, 20.6; IR (film) ν$_{max}$ 3308, 3223, 2905, 2843, 1627, 1496, 1457, 1407, 1358, 1305, 1259, 1157, 1100, 1038, 906, 849 cm$^{-1}$; HRMS Calcd. for C$_{11}$H$_{15}$NO$_4$ (M$^+$): 225.1001. Found: 225.1000.

Silyl ether 42. To a solution of alcohol 41 (23.4 g, 104 mmol) in DMF (350 mL) was added imidazole (9.90 g, 146 mmol), DMAP (635 mg, 5.2 mmol) and TBSCl (17.26 g, 114 mmol). The mixture was left to stand for 3 h before being quenched with anhydrous methanol (30 mL). After 0.25 h, the reaction mixture was diluted with ethyl ether (1 L), washed with h$_2$O (500 mL), NaHCO$_3$ (500 mL) and dried (MgSO$_4$). The mixture was concentrated under reduced pressure and placed under high vacuum (0.03 torr) for 36 h to yield crude silyl ether 42 (37.0 g, 100%) as an off white solid. A small sample was purified by flash chromatography (silica gel, 40→50% ethyl ether in petroleum ether) for the purpose of data collection: White crystals (neat); mp 65°–67.5° C.; R$_f$=0.26 (silica gel, 40% ethyl ether in petroleum ether); $^1$H NMR (500 MHz, CDCl$_3$) δ6.86 (s, 1 h, Ar), 5.05 (q, J=5.1 hz, 1 h, OCHO), 4.79 (d, J=14.1 hz, 1 h, ring benzylic CH$_2$), 4.73 (d, J=14.1 hz, 1 h, ring benzylic CH$_2$), 4.70 (d, J=13.0 hz, 1 h, CH$_2$OTBS), 4.65 (d, J=13.0 hz, 1 h, CH$_2$OTBS), 3.82 (s, 3 h, OCH$_3$), 3.7–3.4 (bs, 2 h, NH$_2$), 1.53 (d, J=5.1 hz, 3 h, CHCH$_3$) 0.95 (s, 9 h, Si$^t$BuMe$_2$), 0.11 (s, 6 h, Si$^t$BuMe$_2$); $^{13}$C NMR (125 MHz, CDCl$_3$) δ143.8, 141.1, 130.4, 117.7, 108.9, 106.8, 96.2, 63.7, 59.3, 56.0, 26.0, 20.6, 18.4, −5.2; IR (film) ν$_{max}$ 3454, 3366, 2934, 2856, 1628, 1497, 1464, 1406, 1364, 1263, 1156, 1103, 1045, 910, 841, 778 cm$^{-1}$; HRMS Calcd. for C$_{17}$H$_{29}$NO$_4$Si (M$^+$): 339.1866. Found: 339.1870.

Urethane 43. To a solution of crude amine 42 (37.0 g, 104 mmol) in methylene chloride (350 mL) was added triethylamine (57.9 mL, 416 mmol), and DMAP (635 mg, 5.2 mmol) and the mixture was cooled to 0° C. Phosgene (65 mL, 1.93M in toluene, 125 mmol) was cautiously added and the reaction mixture was allowed to warm to ambient temperature. After 1 h, methanol (50 mL) was added and the reaction mixture was left to stand for 0.5 h before being diluted with ethyl ether (1 L), washed with 1N hCl (2×300 mL), NaHCO$_3$ (300 mL), NaCl (300 mL) and dried (MgSO$_4$). The mixture was concentrated under reduced pressure and placed under high vacuum (0.03 torr) until the residue solidified. The solid was dissolved in the minimum amount of methylene chloride (ca 30 mL) and petroleum ether (100 mL) was added. After cooling to −20° C. for 24 h, the product was filtered (27.42 g) and the mother liquor was concentrated under reduced pressure and purified by flash chromatography (silica gel, 30% ethyl ether in petroleum ether) to yield a further 2.11 g of urethane 43 (72% for two steps): Colorless rhombohedral crystals (ethyl ether and petroleum ether); mp 85.5°–86.0° C.; R$_f$=0.74 (silica gel, 70% ethyl ether in petroleum ether); $^1$H NMR (500 MHz, CDCl$_3$) δ7.00 (s, 1 h, Ar), 6.4–6.3 (bs, 1 h, NH), 5.17 (q, J=5.0 hz, 1 h, OCHO), 5.00 (bd, J=14.7 hz, 1 h, ring benzylic CH$_2$), 4.71 (d, J=14.7 hz, 1 h, ring benzylic CH$_2$), 4.71 (s, 2 h, CH$_2$OTBS), 3.79 (s, 3 h, OCH$_3$), 3.74 (s, 3 h, OCH$_3$), 1.52 (d, J=5.0 hz, 3 h, CHCH$_3$), 0.96 (s, 9 h, Si$^t$BuMe$_2$), 0.11 (s, 6 h, Si$^t$BuMe$_2$); $^{13}$C NMR (125 MHz, CDCl$_3$) δ155.1, 146.6, 142.9, 127.1, 119.8, 117.9, 108.0, 96.7, 65.1, 59.4, 55.8, 52.7, 25.9, 20.7, 18.4, −5.3; IR (film) ν$_{max}$ 3314, 2950, 2857, 1734, 1614, 1511, 1463, 1408, 1352, 1252, 1079, 907, 842, 777 cm$^{-1}$; HRMS Calcd. for C$_{19}$H$_{31}$NO$_6$Si (M+Cs$^+$): 530.0975. Found: 530.0965. Anal. Calcd. for C$_{19}$H$_{31}$NO$_6$Si: C, 57.4; h, 7.86; N, 3.52. Found: C, 57.18; h, 8.17; N, 3.30.

Quinone monoketal 44. To a solution of 43 (27.4 g, 69.0 mmol) in 1,4-dioxane (260 mL) and ethylene glycol (86 mL) at 0° C. was added ammonium cerium(IV) nitrate (75.7 g, 138 mmol). After 0.2 h the cooling bath was removed and stirring continued for a further 0.25 h. The mixture was then left to stand for a further 1.5 h before being diluted with ethyl ether (1200 mL) and washed with h$_2$O (300 mL). The aqueous phase was extracted with ethyl ether (300 mL) and the combined organic phases were washed with NaHCO$_3$ (3×300 mL), NaCl (300 mL) and dried (MgSO$_4$). After concentration under reduced pressure the residue was redissolved in methylene chloride (200 mL) and silica gel (60 g) was added. The slurry was stirred for 14 h before being filtered and concentrated under reduced pressure. Crystallization from benzene (50 mL) yielded compound 44 (5.44 g). Purification of the mother liquor by flash chromatography (silica gel, 40→60→70% ethyl ether in petroleum ether) yielded a further 2.16 g of 44 (30%): White crystals (benzene); mp 178°–179° C. (dec); R$_f$=0.58 (silica gel, ethyl ether); $^1$H NMR (500 MHz, CDCl$_3$) δ8.65 (bs, 1 h, NH), 6.59 (t, J=2.2 hz, 1 h, vinyl CH), 5.15 (s, 2 h, cyclic allylic CH$_2$), 4.42 (d, J=2.2 hz, 2 h, CH$_2$OTBS), 4.40–4.35 (m, 2 h, ketal), 4.26–4.21 (m, 2 h, ketal), 0.92 (s, 9 h, Si$^t$BuMe$_2$), 0.09 (s, 6 h, Si$^t$BuMe$_2$); $^{13}$C NMR (125 MHz, CDCl$_3$) δ181.2, 151.3, 145.7, 137.2, 132.1, 107.5, 97.4, 66.2, 65.7, 59.1, 25.9, 18.4, −5.4; IR (film) ν$_{max}$ 3234, 3162, 2953, 1739, 1698, 1636, 1480, 1415, 1333, 1255, 1222, 1131, 1052 cm$^{-1}$; HRMS Calcd. for C$_{17}$H$_{25}$O$_6$NSi (M+Cs$^+$): 500.0505. Found: 500.0503.

PMB urethane 45. To a solution of amide 44 (3.45 g, 9.4 mmol) in DMF (47 mL) was added finely ground potassium carbonate (2.59 g, 18.8 mmol) and p-methoxybenzyl bromide (7.05 mL, 2M solution in benzene, 14.1 mmol). The reaction mixture was stirred for 3.5 h before being diluted with ethyl acetate (250 mL), washed with h$_2$O (50 mL), NaCl (50 mL) and dried (MgSO$_4$). Concentration under reduced pressure and purification by flash chromatography (silica gel, 40→50% ethyl ether in petroleum ether) yielded 45 (4.12 g, 90%): Colorless oil; R$_f$=0.53 (silica gel, 70% ethyl ether in petroleum ether); $^1$H NMR (500 MHz, CDCl$_3$) δ7.27 (d, J=8.7 hz, 2 h, Ar), 6.84 (d, J=8.7 hz, 2 h, Ar), 6.64 (t, J=2.2 hz, 1 h, vinyl CH), 4.94 (s, 2 h, benzylic CH$_2$ or cyclic allylic CH$_2$), 4.91 (s, 2 h, benzylic CH$_2$ or cyclic allylic CH$_2$), 4.44 (d, J=2.2 hz, 2 h, CH$_2$OTBS), 4.29–4.21 (m, 4 h, ketal), 3.78 (s, 3 h, OCH$_3$), 0.93 (s, 9 h, Si$^t$BuMe$_2$), 0.09 (s, 6 h, Si$^t$BuMe$_2$); $^{13}$C NMR (125 MHz, CDCl$_3$) δ181.4, 158.9, 152.3, 145.7, 135.4, 132.0, 129.6, 128.5, 113.8, 113.6, 99.8, 64.4, 62.0, 58.7, 55.2, 47.8, 25.8, 18.3, −5.4; IR (CHCl$_3$) ν$_{max}$ 1738, 1689, 1635, 1514, 1418, 1248, 1162, 1132 cm$^{-1}$; HRMS Calcd. for C$_{25}$H$_{33}$O$_7$NSi (M+Cs$^+$): 620.1081. Found: 620.1075.

Allylic alcohol 46. To a solution of silyl ether 45 (2.48 g, 5.09 mmol) in THF (20 mL) in a polypropylene vessel at 0° C. was added hydrogen fluoride-pyridine (7.6 mL) portionwise over 0.2 h. After 1 h the mixture was poured cautiously into a saturated solution of NaHCO$_3$ (250 mL) and diluted with ethyl acetate (250 mL). After stirring for 0.1 h, the layers were separated and the organic phase was washed with NaHCO$_3$ (50 mL) and NaCl (100 mL). The aqueous phases were extracted with methylene chloride (2×100 mL) and the combined organic phases were dried (MgSO$_4$) and concentrated under reduced pressure. The residue was dissolved in methylene chloride (20 mL) and pure alcohol 46 (1.76 g, 93%) was precipitated by the dropwise addition of petroleum ether (40 mL): White crystals (toluene); mp 155.5°–156.5° C. (prior yellowing); R$_f$=0.33 (silica gel, 20% acetone in chloroform); $^1$H NMR (500 MHz, CDCl$_3$) δ7.26 (d, J=8.7 hz, 2 h, Ar), 6.84 (d, J=8.7 hz, 2 h, Ar), 6.59 (t, J=1.6 hz, 1 h, vinyl CH), 4.94 (s, 2 h, benzylic CH$_2$ or cyclic allylic CH$_2$), 4.89 (s, 2 h, benzylic CH$_2$ or cyclic allylic CH$_2$), 4.40 (d, J=1.6 hz, 2 h, CH$_2$OH), 4.31–4.20 (m, 4 h, ketal), 3.78 (s, 3 h, OCH$_3$), 2.3–2.2 (bs, 1 h, OH); $^{13}$C NMR (125 MHz, CDCl$_3$) δ181.9, 158.9, 152.3, 145.9, 134.5, 133.3, 129.4, 128.5, 113.8, 113.5, 99.5, 64.5, 62.0, 59.5, 55.2, 47.8; IR (film) ν$_{max}$ 3438, 2909, 1728, 1690, 1634, 1513, 1415, 1246, 1162, 1135, 732 cm$^{-1}$; HRMS Calcd. for C$_{19}$H$_{19}$NO$_7$ (M+Cs$^+$): 506.0216. Found: 506.0214. Anal. Calcd. for C$_{19}$H$_{19}$NO$_7$: C, 61.12; h, 5.13; N, 3.75. Found: C, 61.11; h, 5.00; N, 3.86.

Epoxide 47. A solution of allylic alcohol 46 (1.75 g, 4.69 mmol) in methylene chloride (7.2 mL) was stirred with pre-dried 4 Å molecular sieves (530 mg) and di-isopropyl-D-tartrate (65 µL, 0.59 mmol) for 4 h. The mixture was cooled to −30° C., treated with titanium tetraisopropoxide (73 µL, 0.47 mmol) and allowed to warm to −3° C. over 0.5 h. The mixture was then re-cooled to −20° C. and treated with tert.-butyl hydroperoxide (2.15 mL, ca 5.5M in methylene chloride, 11.8 mmol). The reaction mixture was stirred for 14 h at 0° C. before being quenched with h$_2$O (10 mL), diluted with ethyl acetate (10 mL) and stirred for 1 h. The mixture was filtered through a pad of Celite® and further diluted with ethyl acetate (150 mL). The layers were separated and the organic phase was washed with Na$_2$S$_2$O$_4$ (2×50 mL, 15% w/w aqueous solution), NaHCO$_3$ (50 mL), NaCl (50 mL) and dried (MgSO$_4$). Concentration under reduced pressure and purification by flash chromatography (silica gel, 10→20% acetone in methylene chloride) gave pure epoxide 47 (1.64 g, 90%) as a white foam: White crystals (methanol); mp 166.0°–166.5° C.; R$_f$=0.37 (silica gel, 20% acetone in chloroform); [α]$_D^{25}$ −41 7 (C=1.10, CHCl$_3$); $^1$H NMR (500 MHz, CDCl$_3$) δ7.24 (d, J=8.7 hz, 2 h, Ar), 6.85 (d, J=8.7 hz, 2 h, Ar), 4.92 (app d, J =14.2 hz, 2 h, benzylic CH$_2$ and allylic CH$_2$), 4.72 (d, J=15.1 hz, 1 h, benzylic CH$_2$ or allylic CH$_2$), 4.69 (d, J=13.9 hz, 1 h, benzylic CH$_2$ or allylic CH$_2$), 4.45–4.33 (m, 3 h, ketal), 4.25–4.17 (m, 1 h, ketal), 4.15 (bd, J=13.5 hz, 1 h, CH$_2$OH), 4.05 (bd, J=13.5 hz, 1 h, CH$_2$OH), 3.79 (s, 3 h, OCH$_3$), 3.77 (s, 1 h, epoxide CH), 2.0–1.9 (bs, 1 h, OH); $^{13}$C NMR (125 MHz, CDCl$_3$) δ188.8, 159.1, 152.3, 145.0, 129.1, 128.7, 114.0, 113.3, 102.3, 65.2, 65.0, 62.2, 58.6, 58.0, 55.7, 55.3, 48.6; IR (film) ν$_{max}$ 3557, 2912, 1737, 1662, 1513, 1412, 1246, 1158, 1076, 1025, 750 cm$^{-1}$; HRMS Calcd. for C$_{19}$H$_{19}$O$_8$N (M+Cs$^+$): 522.0165. Found: 522.0179.

Urethane 48. To a solution of epoxy alcohol 47 (862 mg, 2.20 mmol) in methylene chloride (11 mL) was added triethylamine (400 µL, 2.86 mmol) and phenyl isocyanate (265 µL, 2.42 mmol). After 0.1 h the reaction mixture was diluted with ethyl acetate (100 mL) and washed with 1N hCl (2×30 mL), NaHCO$_3$ (30 mL), NaCl (30 mL) and dried (MgSO$_4$). Concentration under reduced pressure and purification by flash chromatography (silica gel, 80% ethyl ether in petroleum ether then ethyl ether) yielded pure urethane 48 (1.06 g, 94%) as a white foam: White crystals (methylene chloride and ethyl ether); mp 161.0°–164.0 ° C. (prior yellowing); R$_f$=0.43 (silica gel, ethyl ether); [α]$_D^{25}$ −18.4 (c=0.99, CHCl$_3$); $^1$H NMR (500 MHz, CDCl$_3$) δ7.38–7.34 (m, 1 h, Ph), 7.33–7.29 (m, 3 h, Ph), 7.23 (d, J=8.7 hz, 2 h, PMB Ar), 7.10–7.06 (m, 1 h, Ph), 6.85 (bs, 1 h, NH), 6.85 (d, J=8.7 hz, 2 h, PMB Ar), 4.94 (d, J=13.9 hz, 1 h, benzylic CH$_2$, CH$_2$OC(O)NHPh or allylic CH$_2$), 4.91 (d, J=14.0 hz, 1 h, benzylic CH$_2$, CH$_2$OC(O)NHPh or allylic CH$_2$), 4.77 (d, J=12.6 hz, 1 h, benzylic CH$_2$, CH$_2$OC(O)NHPh or allylic CH$_2$), 4.71 (d, J=14.0 hz, 1 h, benzylic CH$_2$, CH$_2$OC(O)NHPh or allylic CH$_2$), 4.70 (d, J=13.9 hz, 1 h, benzylic CH$_2$, CH$_2$OC(O)NHPh or allylic CH$_2$), 4.53 (bd, J=12.6 hz, 1 h, benzylic CH$_2$, CH$_2$OC(O)NHPh or allylic CH$_2$), 4.41–4.30 (m, 3 h, ketal), 4.21–4.16 (m, 1 h, ketal), 3.80 (s, 1 h, epoxide CH), 3.78 (s, 3 h, OCH$_3$); $^{13}$C NMR (125 MHz, CDCl$_3$) δ186.9, 159.0, 152.5, 152.2, 144.7, 137.3, 129.1, 129.0, 128.6, 123.8, 118.6, 113.9, 113.1, 102.0, 65.2, 65.0, 62.2, 59.8, 57.0, 55.2, 48.5; IR (film) ν$_{max}$ 3338, 2964, 2910, 1735, 1665, 1605, 1537, 1515, 1444, 1413, 1384, 1348, 1315, 1219, 1160, 1095, 1065, 1025, 908, 731 cm$^{-1}$; HRMS Calcd. for C$_{26}$H$_{24}$O$_9$N$_2$ (M+Cs$^+$): 641.0536. Found: 641.0555.

Carbonate 49. To a solution of epoxy urethane 48 (1.06 g, 2.02 mmoL) in methylene chloride (10 mL) at 0° C. was added boron trifluoride etherate (281 µL, 2.22 mmoL) and the mixture was allowed to warm to ambient temperature. After 0.3 h, acetic acid (1.0 mL, 50% v/v aqueous solution) and ethyl acetate (10 mL) were added and the mixture was stirred for a further 0.6 h. The mixture was diluted with ethyl acetate (100 mL), washed with h$_2$O (20 mL), NaHCO$_3$ (2×20 mL) and NaCl (20 mL). The aqueous phases were extracted with methylene chloride (2×20 mL) and the combined organic phases were dried (MgSO$_4$). Concentration under reduced pressure and purification by flash chromatography (silica gel, 10→20% acetone in chloroform) gave carbonate 49 (771 mg, 86%): White crystals (methylene chloride/ethyl ether); mp 115°–135° C.; R$_f$=0.75 (silica gel, ethyl acetate); [α]$_D^{25}$ +100.7 (c=0.87, CHCl$_3$); $^1$H NMR (500 MHz, DMSO-d$_6$) δ7.17 (d, J=8.7 hz, 2 h, Ar), 7.01 (d, J=6.1 hz, 1 h, OH), 6.86 (d, J=8.7 hz, 2 h, Ar), 4.99 (d, J=14.0 hz, 1 h, benzylic CH$_2$ or allylic CH$_2$), 4.79 (d, J=14.0 hz, 1 h, benzylic CH$_2$ or allylic CH$_2$), 4.75 (d, J=9.0 hz, 1 h, carbonate CH$_2$), 4.69 (d, J=15.9 hz, 1 h, benzylic CH$_2$ or allylic CH$_2$), 4.65 (d, J=15.9 hz, 1 h, benzylic CH$_2$ or allylic CH$_2$), 4.52 (d, J=9.0 hz, 1 h, carbonate CH$_2$), 4.50 (d, J=6.1 hz, 1 h, CHOH), 4.39–4.25 (m, 2 h, ketal), 4.09–4.04 (m, 2 h, ketal), 3.72 (s, 3 h, OCH$_3$); $^{13}$C NMR (125 MHz, DMSO-d$_6$) δ187.1, 158.2, 153.9, 151.4, 150.0, 129.4, 127.8, 113.6, 105.2, 83.9, 79.2, 72.7, 67.6, 67.4, 66.6, 62.0, 55.0, 48.5; IR (film) ν$_{max}$ 3404, 2967, 2914, 2838, 1806, 1738, 1671, 1627, 1512, 1409, 1382, 1347, 1243, 1173, 1087, 1056, 947, 752 cm$^{-1}$; HRMS Calcd. for C$_{20}$H$_{19}$O$_{10}$N (M+Na$^+$): 456.0907. Found: 456.0903. Anal. Calcd. for C$_{20}$H$_{19}$O$_{10}$N: C, 55.43; h, 4.42; N, 3.23. Found: C, 55.19; h, 4.08; N, 3.17.

THP ether 50. To a solution of alcohol 49 (759 mg, 1.75 mmol) in chloroform (8.8 mL) was added dihydropyran (480 μL, 5.25 mmol) and PPTS (44 mg, 0.18 mmol) and the mixture heated at reflux for 16 h. After cooling to ambient temperature, the mixture was diluted with ethyl acetate (100 mL) and washed with NaHCO$_3$ (30 mL), NaCl (30 mL) and dried (MgSO$_4$). After concentration under reduced pressure, the solid was triturated with ethyl ether (2×20 mL) and purified by flash chromatography (silica gel, 2.5→5% acetone in methylene chloride) to yield the less polar isomer (456 rag) and the more polar isomer (367 mg), (90% total yield of 50).

50 (Less polar isomer): White crystals (methylene chloride/ethyl ether); mp 195.0–197.5 (dec); $R_f$=0.40 (silica gel, 5% acetone in chloroform); $[\alpha]_D^{25}$ +104.8 (C=1.47, CHCl$_3$); $^1$H NMR (500 MHz, CDCl$_3$) δ7.19 (d, J=8.7 hz, 2 h, Ar), 6.84 (d, J =8.7 hz, 2 h, Ar), 5.06 (d, J=14.2 hz, 1 h, benzylic CH$_2$ or allylic CH$_2$), 4.90 (d, J=15.0 hz, 1 h, benzylic CH$_2$ or allylic CH$_2$), 4.90 (d, J=9.1 hz, 1 h, carbonate CH$_2$), 4.75–4.69 (m, 2 h, THP anomeric CH and ketal), 4.66 (d, J=15.0 hz, 1 h, benzylic CH$_2$ or allylic CH$_2$), 4.63 (d, J=14.2 hz, 1 h, benzylic CH$_2$ or allylic CH$_2$), 4.62 (s, 1 h, CHOTHP), 4.46–4.42 (m, 1 h, ketal), 4.28 (d, J=9.1 hz, 1 h, carbonate CH$_2$), 4.20–4.12 (m, 2 h, ketal), 4.05–4.00 (m, 1 h, THP), 3.79 (s, 3 h, OCH$_3$), 3.54–3.47 (m, 1 h, THP), 1.9–1.5 (m, 6 h, THP); $^{13}$C NMR (125 MHz, CDCl$_3$) δ186.1, 159.1, 153.3, 151.5, 151.2, 128.7, 128.5, 114.0, 113.6, 105.1, 102.4, 83.8, 78.0, 68.0, 67.5, 67.3, 65.9, 61.5, 55.2, 49.0, 31.4, 24.8, 21.2; IR (film) $v_{max}$ 2944, 2859, 1816, 1745, 1674, 1628, 1513, 1408, 1245, 1171, 1062, 1034, 952 cm$^{-1}$; HRMS Calcd. for C$_{25}$H$_{27}$O$_{11}$N (M+Cs$^+$): 650.0638. Found: 650.0629.

50 (More polar isomer): White crystals (methylene chloride/ethyl ether); mp 184.0°–185.5° C. (dec); $R_f$=0.28 (silica gel, 5% acetone in chloroform); $[\alpha]_D^{25}$ +19.0 (c=0.97, CHCl$_3$); $^1$H NMR (500 MHz, CDCl$_3$) δ7.17 (d, J=8.7 hz, 2 h, Ar), 6.85 (d, J=8.7 hz, 2 h, Ar), 4.98 (d, J=14.2 hz, 1 h, benzylic CH$_2$ or allylic CH$_2$), 4.90 (obs, 1 h, THP anomeric CH), 4.89 (d, J=15.2 hz, 1 h, benzylic CH$_2$ or allylic CH$_2$), 4.83 (d, J=9.0 hz, 1 h, carbonate CH$_2$), 4.77 (d, J=14.2 hz, 1 h, benzylic CH$_2$ or allylic CH$_2$), 4.76 (d, J=15.2 hz, 1 h, benzylic CH$_2$ or allylic CH$_2$), 4.53 (s, 1 h, CHOTHP), 4.40–4.26 (m, 3 h, ketal and carbonate CH$_2$), 4.17–4.08 (m, 2 h, ketal), 3.93–3.88 (m, 1 h, THP), 3.79 (s, 3 h, OCH$_3$), 3.60–3.55 (m, 1 h, THP), 1.85–1.72 (m, 2 h, THP), 1.65–1.53 (m, 4 h, THP); $^{13}$C NMR (125 MHz, CDCl$_3$) δ186.5, 159.0, 153.6, 151.6, 151.1, 128.4, 128.2, 114.0, 106.1, 100.8, 82.5, 78.0, 67.6, 67.4, 67.3, 63.3, 61.8, 55.2, 49.1, 30.9, 24.6, 19.3; IR (film) $v_{max}$ 2949, 1813, 1745, 1671, 1629, 1513, 410, 1246, 1172, 1065, 1036, 952 cm$^{-1}$; HRMS Calcd. for C$_{25}$H$_{27}$O$_{11}$N (M+Cs$^+$): 650.0638. Found: 650.0621.

Acetonitrile adduct 51. To a solution of tert.-butyl lithium (382 μL, 1.7M in pentane, 0.65 mmol) in THF (2.7 mL) at −78° C. was added acetonitrile (37 μL, 0.70 mmol). After 90 s, the solution was transferred rapidly via cannula to a solution of ketone 50 (more polar isomer) (280 mg, 0.54 mmol) in THF (5.4 mL) at −78° C. After 0.1 h, the reaction was quenched by the addition of a saturated solution of NH$_4$Cl (5 mL), h$_2$O (5 mL) and ethyl acetate (5 mL). After warming to ambient temperature, the mixture was diluted with ethyl acetate (70 mL) and the layers were separated. The organic phase was washed with NaCl (30 mL) and dried (MgSO$_4$). Concentration under reduced pressure and purification by flash chromatography (silica gel, 10→20% acetone in chloroform) gave adduct 51 (279 mg, 92%): White solid; $R_f$=0.30 (silica gel, 20% acetone in chloroform); $[\alpha]_D^{25}$ −37.8 (c=1.95, CHCl$_3$); $^1$H NMR (500 MHz, CDCl$_3$) δ7.20 (d, J=8.7 hz, 2 h, Ar), 6.84 (d, J=8.7 hz, 2 h, Ar), 4.96 (d, J=9.2 hz, 1 h, carbonate CH$_2$), 4.79 (d, J=14.1 hz, 1 h, benzylic CH$_2$ or allylic CH$_2$), 4.78–4.76 (m, 1 h, THP anomeric CH), 4.70 (d, J=15.1 hz, 1 h, benzylic CH$_2$ or allylic CH$_2$), 4.69 (d, J=14.1 hz, 1 h, benzylic CH$_2$ or allylic CH$_2$), 4.68 (d, J=9.2 hz, 1 h, carbonate CH$_2$), 4.62 (d, J=15.1 hz, 1 h, benzylic CH$_2$ or allylic CH$_2$), 4.35–4.30 (m, 3 h, CHOTHP, OH and/or ketal), 4.22–4.12 (m, 3 h, OH and/or ketal), 3.96–3.91 (m, 1 h, THP), 3.79 (s, 3 h, OCH$_3$) 3.58–3.54 (m, 1 h, THP), 3.07 (d, J=17.1 hz, 1 h, CH$_2$CN), 2.90 (d, J=17.1 hz, 1 h, CH$_2$CN), 1.86–1.75 (m, 2 h, THP), 1.65–1.53 (m, 4 h, THP); $^{13}$C NMR (125 MHz, CDCl$_3$) δ158.8, 154.7, 154.6, 134.0, 128.9, 128.2, 128.1, 118.4, 116.1, 113.8, 106.2, 101.5, 86.7, 78.1, 73.2, 67.2, 66.8, 65.6, 63.8, 62.5, 55.2, 47.7, 31.2, 26.3, 24.7, 19.7; IR (film) $v_{max}$ 3382, 2925, 2248, 1808, 1723, 1512, 1246, 1179, 1070, 1032 cm$^{-1}$. HRMS Calcd. for C$_{27}$H$_{30}$O$_{11}$N$_2$ (M+Na$^+$): 581.1747. Found: 581.1760.

Acrylonitrile 52. To a solution of tertiary alcohol 51 (217 mg, 0.389 mmol) in methylene chloride (3.9 mL) was added triethylamine (174 μL, 1.21 mmol), DMAP (4.8 mg, 0.04 mmol) and acetic anhydride (48 μL, 0.51 mmol). The mixture was left to stand for 5 d before being diluted with ethyl acetate (40 mL), washed with 1N hCl (15 mL), NaHCO$_3$ (15 mL), NaCl (15 mL) and dried (MgSO$_4$). Concentration under reduced pressure and purification by flash chromatography (silica gel, 5% acetone in chloroform) yielded 52 (172 mg, 82%): Colorless oil; $R_f$=0.48 (silica gel, 10% acetone in chloroform); $[\alpha]_D^{25}$ −133 (c=4.35, CHCl$_3$); $^1$H NMR (500 MHz, CDCl$_3$) δ7.18 (d, J=8.7 hz, 2 h, Ar), 6.86 (d, J =8.7 hz, 2 h, Ar), 5.63 (s, 1 h, CHCN), 5.27 (d, J=14.1 hz, 1 h, allylic CH$_2$), 5.11 (d, J=9.1 hz, 1 h, carbonate CH$_2$), 5.01 (d, J=14.1 hz, 1 h, allylic CH$_2$), 4.85 (d, J=14.9 hz, 1 h, benzylic CH$_2$), 4.85–4.83 (m, 1 h, THP anomeric CH), 4.78 (d, J=14.9 hz, 1 h, benzylic CH$_2$), 4.43–4.38 (m, 1 h, ketal), 4.30 (s, 1 h, CHOTHP), 4.26–4.22 (m, 1 h, ketal), 4.20–4.11 (m, 2 h, ketal), 4.17 (d, J=9.1 hz, 1 h, carbonate CH$_2$), 3.97–3.93 (m, 1 h, THP), 3.80 (s, 3 h, OCH$_3$), 3.59–3.55 (m, 1 h, THP), 1.82–1.76 (m, 2 h, THP), 1.65–1.55 (m, 4 h, THP); $^{13}$C NMR (125 MHz, CDCl$_3$) δ128.5, 122.1, 114.1, 92.7, 78.9, 69.4, 67.0, 63.9, 63.4, 55.3, 48.3, 47.2, 31.2, 24.7, 19.7; IR (film) $v_{max}$ 2925, 2854, 2213, 1817, 1736, 1613, 1513, 1376, 1246, 1178, 1069, 1034, 950 cm$^{-1}$. HRMS Calcd. for C$_{27}$H$_{28}$O$_{10}$N$_2$ (M+Na$^+$): 563.1642. Found: 563.1660.

Diol 53. To a solution of carbonate 52 (131 mg, 0.25 mmol) in THF (2.5 mL) and ethylene glycol (125 μL) was added lithium hydride (2.0 mg, 0.25 mmol). The reaction mixture was stirred for 1.25 h before being diluted with ethyl acetate (45 mL), washed with h$_2$O (2×10 mL), NaCl (10 mL) and dried (MgSO$_4$). Concentration under reduced pressure and purification by flash chromatography (silica gel, 5→10% acetone in chloroform) gave diol 53 (100 mg, 80%): White solid; $R_f$=0.54 (silica gel, 20% acetone in chloroform); $[\alpha]_D^{25}$ −128 (c=3.45, CHCl$_3$); $^1$H NMR (500 MHz CDCl$_3$) δ7.18 (d, J=8.6 hz, 2 h, Ar), 6.84 (d, J=8.6 hz, 2 h, Ar), 5.88 (s, 1 h, CHCN), 5.39 (d, J=13.9 hz, 1 h, allylic CH$_2$), 5.29 (s, 1 h, THP anomeric CH), 4.92 (d, J =13.9 hz, 1 h, allylic CH$_2$), 4.82 (d, J=15.2 hz, 1 h, benzylic CH$_2$), 4.70 (d, J=15.2 hz, 1 h, benzylic CH$_2$), 4.47–4.45 (m, 1 h, ketal), 4.36–4.34 (m, 1 h, ketal), 4.17–4.07 (m, 3 h, ketal and THP), 3.95 (s, 1 h, CHOTHP), 3.78 (s, 3 h, OCH$_3$), 3.75 (bd, J=11.7 hz, 1 h, CH$_2$OH), 3.72–3.68 (bm, 1 h, CH$_2$OH), 3.57–3.53 (m, 1 h, THP), 2.40 (bs, 1 h, OH), 1.92–1.85 (m, 1 h, THP), 1.83–1.75 (m, 1 h, THP), 1.62–1.50 (m, 4 h, THP); $^{13}$C NMR (125 MHz, CDCl$_3$) δ158.8, 153.5, 153.4, 138.4, 129.5, 128.1, 117.5, 115.8, 113.9, 106.0, 103.7, 93.6, 87.3, 74.7, 67.6, 66.7, 66.6, 65.4, 63.6, 55.2, 47.6, 31.6, 24.4, 21.4; IR (film) $v_{max}$ 3368, 3063, 2950, 2866, 2209, 1730, 1615, 1513, 1421, 1368, 1246, 1180, 1121, 1030, 953, 912, 864, 732 cm$^{-1}$; HRMS Calcd. for $C_{26}H_{30}O_9N_2$ (M+H$^+$): 515.2048. Found: 515.2048.

Aldehyde 54. To a solution of diol 53 (87 mg, 0.17 mmol) in acetonitrile (1.7 mL) was added Dess-Martin periodinane (144 mg, 0.338 mmol) and the mixture was stirred for 30 h. After dilution with ethyl acetate (40 mL) the mixture was filtered through a pad of silica gel, concentrated under reduced pressure and purified by flash chromatography (silica gel, 3→5% acetone in chloroform) to yield hydroxy aldehyde 54 (81 mg, 93%): Colorless oil; $R_f$=0.56 (silica gel, 10% acetone in chloroform); $^1$H NMR (500 MHz, $C_6D_6$) δ9.55 (s, 1 h, CHO), 7.29 (d, J=8.7 hz, 2 h, Ar), 6.82 (d, J=8.7 hz, 2 h, Ar), 5.68 (s, 1 h, CHCN), 5.38 (d, J=14.2 hz, 1 h, allylic CH$_2$), 4.82 (d, J=15.2 hz, 1 h, benzylic CH$_2$), 4.71 (d, J=15.2 hz, 1 h, benzylic CH$_2$), 4.50 (d, J=14.2 hz, 1 h, allylic CH$_2$), 4.03 (dd, J=6.5, 2.8 hz, 1 h, THP anomeric CH), 3.66–3.61 (m, 1 h, ketal), 3.59–3.54 (m, 1 h, ketal), 3.51 (s, 1 h, CHOTHP), 3.42–3.27 (m, 3 h, ketal and THP), 3.30 (s, 3 h, OCH$_3$), 3.12–3.05 (m, 1 h, THP), 1.4–0.9 (m, 6 h, THP); IR (film) $v_{max}$ 3315, 3059, 2925, 2860, 2211, 1733, 1615, 1513, 1436, 1372, 1246, 1183, 1121, 1029, 952, 913, 814, 731 cm$^{-1}$; HRMS Calcd. for $C_{26}H_{28}O_9N_2$ (M+Cs$^+$): 645. Found: 645.

TMS ether 55. To a solution of hydroxy aldehyde 54 (21 mg, 41 μmol) in 1,2-dichloroethane (4 mL) was added 2,6-lutidine (72 μL, 620 μmol) and TMSOTf (79 μL, 410 μmol). The mixture was heated at 70° C. for 4.5 h before being cooled, diluted with ethyl ether (50 mL), washed with CuSO$_4$ (20 mL), NaHCO$_3$ (20 mL) and dried (MgSO$_4$). Concentration under reduced pressure and purification by flash chromatography (silica gel, 10% ethyl acetate in toluene) gave pure silyl ether 55 (14 mg; 60%): Colorless oil; $R_f$=0.29 (silica gel, 70% ethyl ether in petroleum ether); $^1$H NMR (500 MHz, $C_6D_6$) δ9.61 (s, 1 h, CHO), 7.25 (d, J=8.7 hz, 2 h, Ar), 6.79 (d, J=8.7 hz, 2 h, Ar), 5.32 (s, 1 h, CHCN), 5.08 (d, J=14.0 hz, 1 h, allylic CH$_2$), 4.85 (d, J=15.1 hz, 1 h, benzylic CH$_2$), 4.75 (d, J=15.1 hz, 1 h, benzylic CH$_2$), 4.60 (d, J=14.0 hz, 1 h, allylic CH$_2$), 4.24 (dd, J=8.5, 2.2 hz, 1 h, THP anomeric CH), 3.93 (s, 1 h, CHOTHP), 3.74–3.68 (m, 1 h, ketal), 3.58–3.54 (m, 1 h, ketal), 3.30–3.24 (m, 3 h, ketal and THP), 3.29 (s, 3 h, OCH$_3$), 3.03–2.96 (m, 1 h, THP), 1.4–0.9 (m, 6 h, THP), 0.34 (s, 9 h, TMS); IR (film) $v_{max}$ 2929, 2856, 2211, 1734, 1616, 1513, 1424, 1376, 1247, 1180, 1118, 1035, 946, 910, 847 cm$^{-1}$; HRMS Calcd. for $C_{29}H_{36}O_9N_2Si$ (M+Na$^+$): 607.2088. Found: 607.2080.

Acetonitrile adduct 57. To a solution of tert.-butyl lithium (2.07 mL, 1.7M in pentane, 3.52 mmol) in THF (25 mL) at −78° C. was added acetonitrile (200 μL, 3.83 mmol). After stirring for 90 s, a solution of ketone 45 (1.49 g, 3.06 mmol) in THF (2×3 mL) was added and the reaction mixture was stirred for a further 0.1 h before being quenched with a saturated solution of ammonium chloride. The mixture was warmed to ambient temperature and diluted with ethyl acetate (200 mL). The layers were separated and the organic phase was washed with NaCl (40 mL) and dried (MgSO$_4$). Concentration under reduced pressure and purification by flash chromatography (silica gel, 70% ethyl ether in petroleum ether) yielded adduct 57 (1.32 g, 82%): Colorless oil; $R_f$=0.29 (silica gel, 80% ethyl ether in petroleum ether); $^1$H NMR (500 MHz, CDCl$_3$) δ7.26 (d, J=8.7 hz, 2 h, Ar), 6.82 (d, J=8.7 hz, 2 h, Ar), 5.93 (dd, J=1.4, 1.1 hz, 1 h, vinyl CH), 4.91 (d, J=13.5 hz, 1 h, benzylic CH$_2$ or cyclic allylic CH$_2$), 4.84 (d, J=15.2 hz, 1 h, benzylic CH$_2$ or cyclic allylic CH$_2$), 4.75 (d, J=15.2 hz, 1 h, benzylic CH$_2$ or cyclic allylic CH$_2$), 4.75 (s, 1 h, tertiary OH), 4.64 (d, J=13.5 hz, 1 h, benzylic CH$_2$ or cyclic allylic CH$_2$), 4.50 (dd, J=13.5, 1.4 hz, 1 h, CH$_2$OTBS), 4.38 (dd, J=13.5, 1.1 hz, 1 h, CH$_2$OTBS), 4.19–4.05 (m, 4 h, ketal), 3.76 (s, 3 h, OCH$_3$), 2.84 (d, J=16.7 hz, 1 h, CH$_2$CN), 2.75 (d, J=16.7 hz, 1 h, CH$_2$CN), 0.91 (s, 9 h, Si$^t$BuMe$_2$), 0.12 (s, 3 h, Si$^t$BuMe$_2$), 0.12 (s, 3 h, Si$^t$BuMe$_2$); $^{13}$C NMR (125 MHz, CDCl$_3$) δ158.6, 154.6, 137.2, 132.2, 130.3, 128.5, 123.7, 121.0, 115.6, 113.7, 100.0, 69.3, 64.2, 63.8, 62.9, 62.1, 55.1, 47.6, 29.0, 25.7, 18.1, −5.6; IR (film) $v_{max}$ 3383, 2953, 2858, 1702, 1613, 1513, 1463, 1375, 1248, 1147, 1111, 1048, 965, 838, 779, 732 cm$^{-1}$; HRMS Calcd. for $C_{27}H_{36}O_7N_2Si$ (M+H$^+$): 529.2370. Found: 529.2370.

Alkenes 58a and 58b. To a solution of alcohol 57 (1.32 g, 2.50 mmol) in methylene chloride (12.5 mL) was added triethylamine (487 μL, 3.5 mmol), DMAP (31 mg, 0.25 mmol) and trifluoroacetic anhydride (424 μL, 3.0 mmol). After 0.25 h the reaction mixture was diluted with ethyl acetate (150 mL), washed with 1N hCl (40 mL), NaHCO$_3$ (40 mL), NaCl (40 mL) and dried (MgSO$_4$). Concentration under reduced pressure and purification by flash chromatography (silica gel, 1% acetone in chloroform) yielded 58a (960 mg, 75%) and 58b (100 mg, 8%).

58a: Colorless oil; $R_f$=0.58 (silica gel, 5% acetone in chloroform); $^1$H NMR (500 MHz, CDCl$_3$) δ7.27 (d, J=8.7 hz, 2 h, Ar), 6.85 (d, J=8.7 hz, 2 h, Ar), 6.20 (bs, 1 h, ring vinyl CH), 5.48 (s, 1 h, CHCN), 5.27 (s, 2 h, cyclic allylic CH$_2$), 4.87 (s, 2 h, benzylic CH$_2$ ), 4.37 (d, J=1.3 hz, 2 h, CH$_2$OTBS), 4.24–4.19 (m, 4 h, ketal), 3.79 (s, 3 h, OCH$_3$), 0.92 (s, 9 h, Si$^t$BuMe$_2$), 0.10 (s, 6 h, Si$^t$BuMe$_2$); $^{13}$C NMR (125 MHz CDCl$_3$) δ158.8, 153.1, 143.4, 137.7, 132.7, 129.9, 128.6, 126.4, 117.5, 114.9, 113.8, 100.4, 92.0, 64.0, 63.9, 61.6, 55.1, 47.9, 25.7, 18.1, −5.4; IR (film) $v_{max}$ 3057, 2954, 2930, 2901, 2856, 2206, 1735, 1614, 1513, 1382, 1249, 1170, 1144, 963, 840, 778, 733 cm$^{-1}$; HRMS Calcd. for $C_{27}H_{34}O_6N_2Si$ (M+H$^+$): 511.2264. Found: 511.2260.

58b: White crystals (ether); mp 144.5°–147.5° C. (prior yellowing); $R_f$=0.51 (silica gel, 5% acetone in chloroform); $^1$H NMR (500 MHz, CDCl$_3$) δ7.26 (d, J= 8.7 hz, 2 h, Ar), 6.84 (d, J=8.7 hz, 2 h, Ar), 6.47 (dt, J=2.0(t), 1.3(d) hz, 1 h, ring vinyl CH), 5.08 (d, J=1.3 hz, 1 h, CHCN), 4.89 (s, 2 h, benzylic CH$_2$ or cyclic allylic CH$_2$), 4.85 (d, J=2.0 hz, 2 h, CH$_2$OTBS), 4.82 (s, 2 h, benzylic CH$_2$ or cyclic allylic CH$_2$), 4.26–4.16 (m, 4 h, ketal), 3.78 (s, 3 h, OCH$_3$), 0.95 (s, 9 h, Si$^t$BuMe$_2$), 0.14 (s, 6 h, Si$^t$BuMe$_2$); $^{13}$C NMR (125 MHz, CDCl$_3$) δ158.9, 152.6, 142.3, 136.5, 132.6, 129.9, 128.7, 126.3, 117.6, 113.8, 113.6, 100.4, 90.7, 64.0, 63.4, 61.2, 55.3, 48.0, 25.8, 18.3, −5.4; IR (film) $v_{max}$ 3056, 2954, 2930, 2901, 2856, 2206, 1731, 1618, 1513, 1384, 1248, 1170, 1143, 1056, 960, 838 cm$^{-1}$; HRMS Calcd. for $C_{27}H_{34}O_6N_2Si$ (M+H$^+$): 511.2264. Found: 511.2260. Anal. Calcd. for $C_{27}H_{34}O_6N_2Si$: C, 63.51; h, 6.71; N, 5.49. Found: C, 63.30; h, 6.75; N, 5.48.

Allylic alcohol 59. To a solution of silyl ether 58 (242 mg, 0.475 mmol) in THF (4.8 mL) in a polypropylene vessel at 0° C. was added hydrogen fluoride-pyridine (710 μL). After 1 h the mixture was poured cautiously into a saturated solution of NaHCO$_3$ (100 mL) and diluted with ethyl acetate (200 mL). After stirring for 0.1 h, the layers were separated and the organic phase was washed with NaHCO$_3$ (50 mL), NaCl (50 mL) and dried (MgSO$_4$). Concentration under reduced pressure and purification by flash chromatography (silica gel, methylene chloride, then 70% ethyl acetate in petroleum ether) yielded allylic alcohol 59 (181 mg, 96%): White solid; $R_f$=0.45 (silica gel, ethyl acetate); $^1$H NMR (500 MHz, CDCl$_3$) δ7.25 (d, J=8.7 hz, 2 h, Ar), 6.84 (d, J=8.7 hz, 2 h, Ar), 6.19 (s, 1 h, ring vinyl CH), 5.57 (s, 1 h, CHCN), 5.26 (s, 2 h, cyclic allylic CH$_2$), 4.84 (s, 2 h, benzylic CH$_2$), 4.35 (d, J=5.7 hz, 2 h, CH$_2$OH), 4.26–4.17 (m, 4 h, ketal), 3.78 (s, 3 h, OCH$_3$), 2.56 (t, J=5.7 hz, 1 h, OH); $^{13}$C NMR (125 MHz, CDCl$_3$) δ158.9, 153.4, 143.2, 137.5, 132.8, 129.8, 128.7, 128.6, 127.2, 117.6, 115.1, 113.9, 100.3, 92.9, 64.1, 64.0, 61.5, 55.2, 48.0; IR (film) v$_{max}$ 3455, 3058, 2965, 2906, 2839, 2207, 1723, 1615, 1512, 1432, 1381, 1294, 1246, 1169, 1094, 1031, 960, 911, 814, 731 cm$^{-1}$; HRMS Calcd. for C$_{21}$H$_{20}$O$_6$N$_2$ (M+H$^+$): 397.1400. Found: 397.1400.

Epoxide 60. A suspension of allylic alcohol 59 (460 mg, 1.16 mmol) in methylene chloride (2.0 mL) was stirred with pre-dried 4 Å molecular sieves (140 mg) and di-isopropyl-D-tartrate (31 μL, 0.145 mmol) for 4 h. The mixture was cooled to −30° C. and treated with titanium tetraisopropoxide (35 μL, 0.116 mmol). The mixture was allowed to warm to −5° C. over 0.5 h before being re-cooled to −10° C. and treated with tert.-butyl hydroperoxide (422 μL, ca 5.5M in methylene chloride, 2.32 mmol). The reaction mixture was stirred for 14 h at 0° C. before being quenched with h$_2$O (2 mL), diluted with ethyl acetate (5 mL) and stirred for 1 h. The mixture was filtered through a pad of Celite® and further diluted with ethyl acetate (100 mL). The layers were separated and the organic phase was washed with Na$_2$S$_2$O$_4$ (2×30 mL, 15% w/w aqueous solution), NaHCO$_3$ (30 mL), NaCl (30 mL) and dried (MgSO$_4$). Concentration under reduced pressure and purification by flash chromatography (silica gel, 70% ethyl acetate in petroleum ether) gave pure epoxide 60 (410 mg, 86%): White solid; R$_f$=0.45 (silica gel, ethyl acetate); [α]$_D^{25}$ −298 (c=0.99, CHCl$_3$); $^1$H NMR (500 MHz, CDCl$_3$) δ7.23 (d, J=8.7 hz, 2 h, Ar), 6.85 (d, J=8.7 hz, 2 h, Ar), 5.66 (s, 1 h, CHCN), 5.06 (d, J=13.9 hz, 1 h, allylic CH$_2$), 4.97 (d, J=13.9 hz, 1 h, allylic CH$_2$), 4.92 (d, J=15.0 hz, 1 h, benzylic CH$_2$), 4.54 (d, J=15.0 hz, 1 h, benzylic CH$_2$), 4.38–4.27 (m, 3 h, ketal), 4.22–4.17 (m, 1 h, ketal), 4.15 (d, J=12.7 hz, 1 h, CH$_2$OH), 3.85 (d, J=12.7 hz, 1 h, CH$_2$OH), 3.79 (s, 3 h, OCH$_3$), 3.62, (s, 1 h, epoxide CH), 2.4–2.3 (bs, 1 h, OH); $^{13}$C NMR (125 MHz, CDCl$_3$) δ159.0, 153.1, 149.1, 136.2, 129.4, 128.7, 116.4, 114.7, 113.9, 103.3, 95.6, 64.8, 60.7, 60.3, 57.6, 55.7, 55.2, 48.6; IR (film) v$_{max}$ 3450, 3069, 2963, 2910, 2214, 1725, 1628, 1512, 1425, 1378, 1290, 1245, 1161, 1023, 910, 817, 730 cm$^{-1}$; HRMS Calcd. for C$_{21}$H$_{20}$O$_7$N$_2$ (M+H$^+$): 413.1349. Found: 413.1350.

Aldehyde 61. To a solution of epoxy alcohol 60 (410 mg, 0.955 mmol) in methylene chloride (10 mL) was added Dess-Martin periodinane (844 mg, 1.91 mmol) and the mixture was stirred at ambient temperature for 36 h. The mixture was filtered through a pad of Celite®, concentrated under reduced pressure and purified by flash chromatography (silica gel, 70→80% ethyl acetate in petroleum ether) to yield aldehyde 61 (404 mg, 99%): White solid; R$_f$=0.41 (silica gel, ethyl acetate); $^1$H NMR (500 MHz, C$_6$D6) δ8.33 (s, 1 h, CHO), 7.26 (d, J=8.6 hz, 2 h, Ar), 6.74 (d, J=8.6 hz, 2 h, Ar), 5.61 (s, 1 h, CHCN), 5.02 (d, J=14.9 hz, 1 h, allylic CH$_2$), 4.79 (d, J=14.1 hz, 1 h, benzylic CH$_2$), 4.65 (d, J=14.1 hz, 1 h, benzylic CH$_2$), 4.36 (d, J=14.9 hz, 1 h, allylic CH$_2$), 3.30–3.10 (m, 4 h, ketal), 3.27 (s, 3 h, OCH$_3$), 2.91, (s, 1 h, epoxide CH); $^{13}$C NMR (125 MHz, CDCl$_3$) δ192.6, 159.2, 153.1, 143.1, 135.4, 129.2, 128.8, 116.2, 115.2, 114.1, 114.0, 99.0, 65.2, 65.1, 64.9, 64.6, 57.1, 56.5, 55.3, 53.7, 48.8, 29.2; IR (film) v$_{max}$ 3439, 3075, 2911, 2839, 2214, 1729, 1626, 1513, 1425, 1380, 1246, 1159, 1023, 944, 816, 755 cm$^{-1}$.

Alkyne 62. To a solution of dimethyl diazomethylphosphonate, (52 mg, 0.35 mmol) in THF (2.0 mL) at −78° C. was added $^n$butyl lithium (119 μL, 2.5M in hexane, 298 μmol). After 0.1 h, a solution of aldehyde 61 (101 mg, 0.246 mmol) in THF (0.6 mL) was added via cannula. After a further 0.25 h the mixture was allowed to warm to 0° C. over 3 h and quenched with a saturated aqueous solution of NH$_4$Cl. The mixture was diluted with ethyl acetate (60 mL) and the layers were separated. The organic phase was washed with NaCl (20 mL) and dried (MgSO$_4$). Concentration under reduced pressure and purification by flash chromatography (silica gel, 50% ethyl acetate in petroleum ether) yielded alkyne 62 (50 mg, 57% accounting for 13 mg of recovered starting material): White solid; R$_f$=0.40 (silica gel, ethyl ether); [α]$_D^{25}$ −279.0 (C=0.13, CHCl$_3$); $^1$H NMR (500 MHz, CDCl$_3$) δ7.23 (d, J=8.6 hz, 2 h, Ar), 6.85 (d, J=8.6 hz, 2 h, Ar), 6.15 (s, 1 h, CHCN), 5.09 (d, J=14.0 hz, 1 h, allylic CH$_2$), 4.96 (d, J=14.0 hz, 1 h, allylic CH$_2$), 4.92 (d, J=15.0 hz, 1 h, benzylic CH$_2$), 4.52 (d, J=15.0 hz, 1 h, benzylic CH$_2$), 4.38–4.33 (m, 3 h, ketal), 4.27–4.20 (m, 1 h, ketal), 3.82 (s, 1 h, epoxide CH), 3.79 (s, 3 h, OCH$_3$), 2.78 (s, 1 h, CCH); $^{13}$C NMR (125 MHz, CDCl$_3$) δ159.1, 152.7, 147.0, 135.9, 129.3, 128.8, 116.2, 114.0, 113.3, 102.8, 97.6, 77.9, 75.5, 65.0, 64.6, 59.8, 55.2, 50.8, 48.6; IR (film) v$_{max}$ 3270, 3016, 2912, 2839, 2215, 2128, 1733, 1629, 1514, 1421, 1380, 1247, 1150, 1019, 755 cm$^{-1}$; HRMS Calcd. for C$_{22}$H$_{18}$O$_6$N$_2$ (M+H$^+$): 407.1243. Found: 407.1240.

Methyl ether 63. To a solution of epoxide 62 (11 mg, 27 μmol) in methanol (0.5 mL) was added sulfuric acid (10 μL, 36N) and the solution heated at 60° C. for 1 h. After cooling to ambient temperature, the solution was diluted with ethyl acetate (40 mL), washed with NaHCO$_3$ (15 mL), NaCl (15 mL) and dried (MgSO$_4$). Concentration under reduced pressure and purification by flash chromatography (silica gel, 80% ethyl ether in petroleum ether then ethyl ether) gave methyl ether 63 (8.5 mg, 72%): Colorless oil; R$_f$=0.36 (silica gel, ethyl ether); $^1$H NMR (500 MHz, C$_6$D6) δ7.26 (d, J=8.7 hz, 2 h, Ar), 6.76 (d, J=8.7 hz, 2 h, Ar), 5.61 (s, 1 h, CHCN), 5.00 (d, J=15.1 hz, 1 h, benzylic CH$_2$ or allylic CH$_2$), 4.90 (d, J=13.6 hz, 1 h, benzylic CH$_2$ or allylic CH$_2$), 4.84 (d, J=13.6 hz, 1 h, benzylic CH$_2$ or allylic CH$_2$), 4.65 (d, J=15.1 hz, 1 h, benzylic CH$_2$ or allylic CH$_2$), 3.70 (d, J=2.5 hz, 1 h, CHOH), 3.29 (s, 3 h, PMB OCH$_3$), 3.24–3.18 (m, 2 h, ketal), 3.08–3.03 (m, 1 h, ketal), 2.99–2.93 (m, 1 h, ketal), 2.91 (s, 3 h, tertiary OCH$_3$), 2.45 (d, J=2.5 hz, 1 h, OH), 2.07 (s, 1 h, CCH); $^{13}$C NMR (125 MHz, C$_6$D$_6$) δ159.2, 152.9, 150.3, 137.3, 130.1, 128.7, 127.9, 116.3, 113.8, 111.8, 104.5, 96.7, 79.0, 78.7, 77.9, 73.6, 64.3, 64.2, 63.7, 54.4, 52.4, 47.7; IR (film) v$_{max}$ 3445, 3263, 2925, 2855, 2214, 2114, 1726, 1620, 1513, 1458, 1422, 1376, 1246, 1179, 1089, 1023 cm$^{-1}$; HRMS Calcd. for C$_{23}$H$_{22}$O$_7$N$_2$ (M+H$^+$): 439.1505. Found: 439.1512.

Diol 64. To a solution of epoxide 62 (50 mg, 0.12 mmol) in tert.-butanol (600 μL) was added sulfuric acid (600 μL, 2N aqueous solution, 0.60 mmol). The vessel was evacuated (20 torr) and flushed with argon three times. The reaction mixture was then heated under argon at 90° C. for 1.5 h before being cooled to ambient temperature and diluted with ethyl acetate (30 mL). The mixture was washed with NaHCO$_3$ (15 mL), NaCl (15 mL) and dried (MgSO$_4$). Concentration under reduced pressure and purification by flash chromatography (silica gel, ethyl ether, then ethyl acetate) yielded epoxide 62 (26 mg) and diol 64 (16 mg) (65% based on recovered starting material): White solid; R$_f$=0.48 (silica gel, ethyl acetate); [α]$_D^{25}$ −141.4 (c=0.42, CHCl$_3$); $^1$H NMR (500 MHz, CDCl$_3$) δ7.24 (d, J=8.7 hz, 2 h, Ar), 6.86 (d, J =8.7 hz, 2 h, Ar), 5.94 (s, 1 h, CHCN), 5.12 (d, J=13.6 hz, 1 h, allylic CH$_2$), 5.07 (d, J=13.6 hz, 1 h, allylic CH$_2$), 4.91 (d, J=15.0 hz, 1 h, benzylic CH$_2$), 4.76 (d, J=15.0 hz, 1 h, benzylic CH$_2$), 4.36–4.30 (m, 2 h, ketal), 4.23–4.17 (m, 2 h, ketal), 3.82 (d, J=9.2 hz, 1 h, CHOH), 3.80 (s, 3 h, OCH$_3$), 3.63 (bs, 1 h, tertiary OH), 2.87 (d, J=9.2 hz, 1 h, CHOH), 2.64 (s, 1 h, CCH); $^{13}$C NMR (125 MHz, CDCl$_3$) δ159.0, 153.3, 151.3, 138.5, 129.5, 128.7, 128.5, 116.7, 114.0, 104.7, 93.5, 79.5, 78.9, 76.4, 71.5, 67.3, 65.8, 64.2, 55.3, 48.0; IR (film) v$_{max}$ 3422, 3280, 2924, 2854, 2214, 2114, 1714, 1617, 1513, 1377, 1246, 1179, 1024 cm$^{-1}$; HRMS Calcd. for C$_{22}$H$_{20}$O$_7$N$_2$ (M+H$^+$): 425.1349. Found: 425.1350.

Bis silyl ether 65. To a solution of diol 64 (16 mg, 35 μmol) in methylene chloride (500 μL) was added pyridine (14 μL, 180 μmol) and TESOTf (24 μL, 110 μmol). After 1.5 h the reaction mixture was diluted with ethyl ether (30 mL), washed with CuSO$_4$ (10 mL), NaHCO$_3$ (10 mL) and dried (MgSO$_4$). Concentration under reduced pressure and purification by flash chromatography (silica gel, 30→40% ethyl ether in petroleum ether) gave bis silyl ether 65 (24 mg, 98%): Colorless oil; R$_f$=0.33 (silica gel, 40% ethyl ether in petroleum ether); $^1$H NMR (500 MHz, CDCl$_3$) δ7.24 (d, J=8.7 hz, 2 h, Ar), 6.83 (d, J=8.7 hz, 2 h, Ar), 5.93 (s, 1 h, CHCN), 5.24 (d, J=13.7 hz, 1 h, allylic CH$_2$), 4.93 (d, J=13.7 hz, 1 h, allylic CH$_2$), 4.92 (d, J=15.0 hz, 1 h, benzylic CH$_2$), 4.81 (d, J=15.0 hz, 1 h, benzylic CH$_2$), 4.11–4.01 (m, 4 h, ketal), 3.79 (s, 4 h, OCH$_3$ and CHOTES), 2.79 (s, 1 h, CCH), 0.96–0.90 (m, 18 h, Si(CH$_2$CH$_3$)$_3$), 0.66–0.60 (m, 12 h, Si(CH$_2$CH$_3$)$_3$); IR (film) v$_{max}$ 3267, 2955, 2912, 2879, 2211, 2114, 1733, 1616, 1513, 1459, 1417, 1376, 1245, 1176, 1136, 1012, 740 cm$^{-1}$; HRMS Calcd. for C$_{34}$H$_{48}$O$_7$N$_2$Si$_2$ (M+H$^+$): 653.3078. Found: 653.3080.

The compounds discussed hereinabove are particularly useful in preparing DNA cleaving aglycons and chimeric antibiotics that exhibit in vitro DNA cleaving activity as well as activity against microorganisms such as *Escherichia coli*, *Klebsiella pneumonia*, *Staphyloccus aureus*, and *Saccharomyces cerevisiae*. These chimers have biological activities similar to those exhibited by calicheamicin and esperamicin. Exemplary chimer syntheses are discussed hereinafter.

A chimeric antibiotic can be utilized as an active agent in an aqueous pharmaceutical composition in which it is dissolved or dispersed. The chimer is thus dissolved or dispersed in a pharmaceutically tolerable diluent such as water, water/ethanol, normal saline or a buffered aqueous solution such as phosphate-buffered saline or within vesicles as are well known. Exemplary further diluents can be found in *Remmington's Pharmaceutical Sciences*, Mack Publishing Co., Easton, Pa. (1980).

The chimeric antibiotic is present in such a pharmaceutical composition in an amount effective to achieve a desired beneficial result. For example, where in vitro DNA cleavage is the desired result, a compound of the invention can be utilized in an amount sufficient to provide a concentration of about 1.0 to about 500 micromolar (μM) with a DNA concentration of about 0.02 μg/μl. As a cytotoxic (anti-tumor) agent, an effective amount of a chimer is about 0.2 to about 15 μg per kilogram of body weight. For use as an antimicrobial agent, a chimer is utilized at about 0.01 to about 50 μg/ml. The particular concentration or dosage can vary with the particular chimer (both as to oligosaccharide and aglycon) utilized as well as the particular target; i.e., DNA, tumor, microbe, as is well known.

Particular antimicrobial and anti-tumor assays can be carried out as described in U.S. Pat. No. 4,837,206, whose disclosures are incorporated by reference, and U.K. patent application G.B. 2,179,649A. DNA cleavage can be assayed as discussed in Nicolaou et al., *J. Am. Chem. Soc.*, 110:7247 j(1988) or Zein et al., *Science*, 240:1198 (1988).

The foregoing specification and the examples contained herein are intended as illustrative of the present invention but are not to be taken as limiting. Numerous variations and modifications may be effected without departing from the true spirit and scope of the present invention.

We claim:

1. A compound represented by the formula

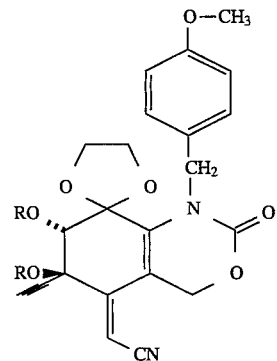

where R is hydrogen or a leaving group.

2. The compound of claim 1 wherein R is hydrogen.

3. The compound of claim 1 wherein R is a leaving group.

4. The compound of claim 3 wherein the leaving group is a triethylsilyl group.

* * * * *